(12) United States Patent
Metcalf et al.

(10) Patent No.: US 9,993,490 B2
(45) Date of Patent: Jun. 12, 2018

(54) PHOSPHONIC ACID COMPOUNDS AND SCREENING METHOD

(71) Applicant: The Board of Trustees of The University of Illinois, Urbana, IL (US)

(72) Inventors: William W. Metcalf, Savoy, IL (US); Kou-San Ju, Champaign, IL (US); Jiangtao Gao, Fuzhou (CN); James R. Doroghazi, Urbana, IL (US); Wilfred A. van der Donk, Champaign, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days. days.

(21) Appl. No.: 15/326,529

(22) PCT Filed: Jul. 21, 2015

(86) PCT No.: PCT/US2015/041344
§ 371 (c)(1),
(2) Date: Jan. 16, 2017

(87) PCT Pub. No.: WO2016/014539
PCT Pub. Date: Jan. 28, 2016

(65) Prior Publication Data
US 2017/0202863 A1 Jul. 20, 2017

Related U.S. Application Data

(60) Provisional application No. 62/027,381, filed on Jul. 22, 2014.

(51) Int. Cl.
| | | |
|---|---|---|
| *A61K 31/66* | (2006.01) | |
| *A61K 31/662* | (2006.01) | |
| *C07F 9/165* | (2006.01) | |
| *C07F 9/24* | (2006.01) | |
| *C07F 9/38* | (2006.01) | |

(52) U.S. Cl.
CPC ............ *A61K 31/662* (2013.01); *A61K 31/66* (2013.01); *C07F 9/1651* (2013.01); *C07F 9/2483* (2013.01); *C07F 9/3808* (2013.01)

(58) Field of Classification Search
CPC .... C07F 9/1651; C07F 9/3808; C07F 9/2483; A61K 31/66
USPC .......................... 514/112, 119, 121, 126, 129
See application file for complete search history.

(56) References Cited

U.S. PATENT DOCUMENTS 3,629,395 A * 12/1971 Litchfield, et al. ...... A23G 4/06
424/48
4,268,503 A * 5/1981 Imanaka ................ A61K 31/66
424/114

FOREIGN PATENT DOCUMENTS

| WO | 97-31659 A1 | 9/1997 |
|---|---|---|
| WO | 00-29596 A1 | 5/2000 |

OTHER PUBLICATIONS

Ju et al., "Genomics-enabled discovery of phosphonate natural products and their biosynthetic pathways", J. Ind. Microbial. Biotechnol., Epub. Nov. 2013, vol. 41, pp. 345-356.
Yu et al., "Diversity and abundance of phosphonate biosynthetic genes in nature", PNAS, 2013, vol. 110, No. 51, pp. 20759-20764.
Metcalf et al., "Biosynthesis of Phosphonic and Phosphinic Acid Natural Products", Annu. Rev. Biochem., 2009, vol. 78, pp. 65-94.
Quinn et al., "Carbon-phosphorus bond cleavage by Gram-positive and Gram-negative soil bacteria", Appl. Microbiol. Biotechnol., 1989, vol. 31, pp. 283-287.
PCT International Search Report and Written Opinion dated Jan. 4, 2016 from corresponding Application No. PCT/US2015/041344, 15 pages.
Cragg et al., "Natural products: a continuing source of novel drug leads", Biochim. Biophys. Acta 1830 (2013) 3670-3695.
Bachmann et al., "Microbial genome mining for accelerated natural products discovery: is a renaissance in the making?", J. Ind. Microbiol. Biotechnol. 41, 175-184 (2014).
Challis, "Genome mining for novel natural product discovery.", J. Med. Chem. 51, 2618-2628 (2008).
Bode et al., "The impact of bacterial genomics on natural product research. Angew. Chem. Int. Ed. 44, 6828-6846 (2005)."
Berdy, J., "Thoughts and facts about antibiotics: where we are now and where we are heading.", J. Antibiot. 65, 385-395 (2012).
Eliot et al., "Cloning, expression, and biochemical characterization of Streptomyces rubellomurinus genes required for biosynthesis of antimalarial compound FR900098.", Chem. Biol. 15, 765-770 (2008).
Blodgett et al., "Molecular cloning, sequence analysis, and heterologous expression of the phosphinothricin tripeptide biosynthetic gene cluster from Streptomyces viridochromogenes DSM 40736.", Antimicrob. Agents Chemother. 49, 230-240 (2005).
Woodyer et al., "Heterologous production of fosfomycin and identification of the minimal biosynthetic gene cluster.", Chem. Biol. 13, 1171-1182 (2006).

(Continued)

*Primary Examiner* — Raymond J Henley, III
(74) *Attorney, Agent, or Firm* — Dilworth IP LLC

(57) ABSTRACT

The present invention relates to pharmaceutical compositions comprising a phosphonic acid compound, such as a natural product. Such compounds can include, such as an antibiotic or compound with other activity, derived from an *Actinobacteria* strain having a gene encoding pepM (phosphoenolpyruvate phosphomutase) or a pepM-dependent biosynthetic pathway. The present invention also relates to methods for treating or preventing or reducing the risk of a bacterial infection by administering a therapeutically effective or prophylactically effective amount of a phosphonic acid antibiotic, or a pharmaceutical composition containing such an antibiotic, to a patient or subject in need thereof. The present invention further relates to methods for isolating, purfying, and identifying such phosphonic acid compounds from *Actinobacteria* strains.

3 Claims, 6 Drawing Sheets

(56) References Cited

OTHER PUBLICATIONS

Borisova et al., "Biosynthesis of rhizocticins, antifungal phosphonate oligopeptides produced by Bacillus subtillis ATCC6633.", Chem. Biol. 17, 28-37 (2010).
Circello et al., "The antibiotic dehydrophos is converted to a toxic pyruvate analog by peptide bond cleavage in *Salmonella enterica*.", Antimicrob. Agents Chemother. 55, 3357-3362 (2011).
Evans et al., "Discovery of the antibiotic phosacetamycin via a new mass spectrometry-based method for phosphonic acid detection.", ACS Chem. Biol. 8, 908-913 (2013).
Nielsen et al., "Phosphorus-31 nuclear magnetic resonance chemical shifts of phosphorus compounds.", J. Chem. Eng. Data 9, 167-170 (1964).
Takahashi, "Phosphonothrixin, a novel herbicidal antibiotic produced by *Saccharothrix* sp. ST-888. I. Taxonomy, fermentation, isolation and biological properties.", J. Antibiot. 48, 1124-1129 (1995).
Okuhara et al., Studies on new phosphonic acid antibiotics. I. FR-900098, isolation and characterization. J. Antibiot. 33, 13-17 (1980).
Okuhara et al., Studies on new phosphonic acid antibiotics. III. Isolation and characterization of FR-31564, FR-32863 and FR-33289. J. Antibiot. 33, 24-28 (1980).
Blodgett et al., Unusual transformations in the biosynthesis of the antibiotic phosphinothricin tripeptide. Nat. Chem. Biol. 3, 480-485 (2007).
Maehr et al., Antimetabolites produced by microorganisms. 8. N5-hydroxy-L-arginine, a new naturally occurring amino acid. J. Antibiot. 26, 284-288 (1973).
Perlman et al., Microbial production of vitamin B12 antimetabolites. I. N5-hydroxy-L-arginine from Bacillus cereus 439. J. Antibiot. 27, 826-832 (1974).
Fischer et al., [Metabolic products of microorganisms. 118. Delta-N-hydroxy-L-arginine, an amino acid antagonist from Nannizzia gypsea]. Arch. Mikrobiol. 91, 203-220 (1973).
Atherton et al., Antibacterial activity and mechanism of action of phosphonopeptides based on aminomethylphosphonic acid. Antimicrob. Agents Chemother. 22, 571-578 (1982).
Cioni et al., Cyanohydrin Phosphonate Natural Product from Streptomyces regensis. J. Nat. Prod. 77, 243-249 (2014).
Halkier et al., Biology and biochemistry of glucosinolates. Annu. Ren. Plant Biol. 57, 303-333 (2006).
Seto et al., Studies on the biosynthesis of bialaphos (SF-1293). 2. Isolation of the first natural products with a C—P—H bond and their involvement in the C—P—C bond formation. J. Antibiot. 36, 96-98 (1983).
Yu et al., Purification and characterization of phosphonoglycans from *Glycomyces* sp. strain NRRL B-16210 and Stackebrandtia nassauensis NRRL B-16338. J. Bacteriol. 196, 1768-1779 (2014).
Doroghazi et al., A roadmap for natural product discovery based on large-scale genomics and metabolomics. Nat. Chem. Biol., Submitted (2014).
PCT International Report on Patentability dated Jan. 24, 2017 from corresponding application No. PCT/US2015/041344, 8 pages.
Stanier et al., The aerobic pseudomonads: a taxonomic study. J. Gen. Microbiol. 43, 159-271 (1966).
Doroghazi et al., Genome sequences of three tunicamycin-producing streptomyces strains, S. chartreusis NRRL 12338, S. chartreusis NRRL 3882, and S. lysosuperificus ATCC 31396. J. Bacteriol. 193, 7021-7022 (2011).
Hyatt et al., Prodigal: prokaryotic gene recognition and translation initiation site identification. BMC Bioinformatics 11, 119 (2010).
Peng et al., IDBA-UD: a de novo assembler for singlecell and metagenomic sequencing data with highly uneven depth. Bioinformatics 28, 1420-1428 (2012).
Chen et al., Structure and kinetics of phosphonopyruvate hydrolase from *Variovorax* sp. Pal2: new insight into the divergence of catalysis within the PEP mutase/isocitrate lyase superfamily. Biochemistry 45, 11491-11504 (2006).

Tamura et al., MEGA6: Molecular Evolutionary Genetics Analysis version 6.0. Mol. Biol. Evol. 30, 2725-2729 (2013).
Price et al., FastTree 2-approximately maximum-likelihood trees for large alignments. PLoS One 5, e9490 (2010).
Kurtz et al., Versatile and open software for comparing large genomes. Genome Biol. 5, R12 (2004).
Schloss et al., Introducing mothur: open-source, plafformindependent, community-supported software for describing and comparing microbial communities. Appl. Environ. Microbial. 75, 7537-7541 (2009).
Colwell, et al., Models and estimators linking individual-based and sample-based rarefaction, extrapolation, and comparison of assemblages. J. Plant Ecol. 5, 3-21 (2012).
Serves et al., Reaction of tris(trimethylsilyl) phosphite with epoxides and glycidol derivatives. Phosphorus, Sulfur Silicon Relat. Elem. 107, 27-31 (1995).
Tone et al., Preparation of 1-hydroxy-2-aminoethylphosphonic acid and its alkyl-substituted derivatives. Chem. Lett. 7, 1349-1350 (1978).
Marfey, Determination of D-amino acids. 2. Use of a bifunctional reagent, 1,5-difluoro-2,4-dinitrobenzene. Carlsberg Res. Commun. 49, 591-596 (1984).
Baer et al., Phosphonic acid analogues of carbohydrate metabolites. I. Synthesis of L-and D-dihydroxypropylphosphonic acid. Can. J. Biochem. 47, 955-960 (1969).
Liu et al., Rapid PCR amplification of minimal enediyne polyketide synthase cassettes leads to a predictive familial classification model. Proc. Natl. Acad. Sci. USA 100, 11959-11963 (2003).
Krug et al., (2014) Secondary metabolomics: the impact of mass spectrometry-based approaches on the discovery and characterization of microbial natural products. Nat Prod Rep 31(6):768-783.
Forseth et al., (2011) NMR-spectroscopic analysis of mixtures: from structure to function. Curr Opin Chem Biol 15 (1):38-47.
Hove-Jensen et al., (2014) Utilization of glyphosate as phosphate source: biochemistry and genetics of bacterial carbon-phosphorus lyase. Microbiol Mol Biol Rev 78(1):176-197.
Hakala et al., (1956) Lactic dehydrogenase. II. Variation of kinetic and equilibrium constants with temperature. J Biol Chem 221(1):191-209.
Philmus et al., (2009) Substrate specificity and scope of MvdD, a GRASP-like ligase from the microviridin biosynthetic gene cluster. ACS Chem Biol 4(6):429-434.
Koehn et al., (2005) The evolving role of natural products in drug discovery. Nat Rev Drug Discov 4(3):206-220.
Brotz-Oesterhelt et al., (2010) Postgenomic strategies in antibacterial drug discovery. Future Microbiol 5 (10):1553-1579.
Baltz, (2006) Marcel Faber Roundtable: is our antibiotic pipeline unproductive because of starvation, constipation or lack of inspiration? J Ind Microbiol Biotechnol 33(7):507-513.
Abdelmohsen et al., (2015) Elicitation of secondary metabolism in actinomycetes. Biotechnol Adv Jun. 15. DOI:10.1016/j.biotechadv.2015.06.003.
Lin et al., (2015) Identification of the biosynthetic gene cluster for the herbicide phosphonothrixin in *Saccharothrix* sp. ST-888. J Antibiot (Tokyo) 68(5):357-359.
Yamazaki et al., (1995) NMR Pulse Schemes for the Sequence-Specific Assignment of Arginine Guanidino N-15 and H-1 Chemical-Shifts in Proteins. J. Am. Chem. Soc. 117(12):3556-3564.
Platzer et al., (2014) pH-dependent random coil (1)H, (13)C, and (15)N chemical shifts of the ionizable amino acids: a guide for protein pK a measurements. J. Biomol. NMR 60(2-3):109-129.
Yavari et al., (1978) Differential rates of proton exchange for the guanidinium nitrogens of L-arginine determined by natural-abundance nitrogen-15 nuclear magnetic resonance spectroscopy. Biochem. Biophys. Res. Commun. 83 (2):635-640.
Clement et al., (1994) Synthesis of 15N omega-hydroxy-L-arginine and ESR and 15N-NMR studies for the elucidation of the molecular mechanism of enzymic nitric oxide formation from Larginine. Arch. Pharm. (Weinheim) 327 (12):793-798.
Bush et al., (2012) Study of the fragmentation of arginine isobutyl ester applied to arginine quantification in Aedes aegypti mosquito excreta. J. Mass. Spectrom. 47(10):1364-1371.

(56) References Cited

OTHER PUBLICATIONS

Gehrig et al., (2004) Fragmentation pathways of N(G)-methylated and unmodified arginine residues in peptides studied by ESI-MS/MS and MALDI-MS. J. Am. Soc. Mass. Spectrom. 15(2):142-149.

Shek et al., (2006) Fragmentations of protonated arginine, lysine and their methylated derivatives: concomitant losses of carbon monoxide or carbon dioxide and an amine. J. Phys. Chem. A 110(27):8282-8296.

* cited by examiner

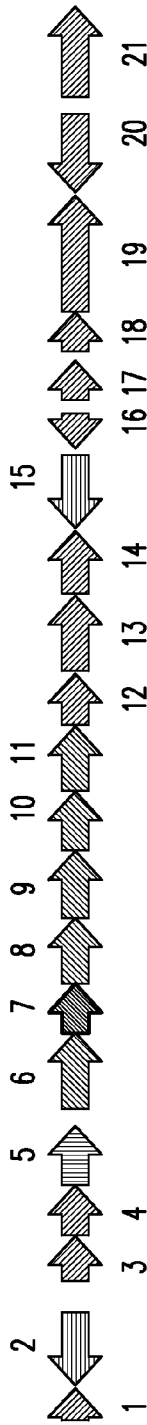

FIG. 3

| No. | ANNOTATION |
|---|---|
| 1 | NUDIX family phosphohydrolase |
| 2 | Carboxlate-amine ligase |
| 3 | Hypothetical |
| 4 | Nucleoside diphosphate kinase |
| 5 | Oxidoredutase |
| 6 | 2-Hydroxyethylphosphonate dioxygenase |
| 7 | Phosphoenolpyruvate mutase |
| 8 | Phosphonopyruvate decarboxylase |
| 9 | Phosphonoacetaldehyde dehydrogenase |
| 10 | D-3-Phosphoglycerate dehydrogenase |
| 11 | Aspartate transaminase |

| No. | ANNOTATION |
|---|---|
| 12 | Hypothetical |
| 13 | MFS transporter |
| 14 | Hypothetical |
| 15 | D-Alanyl-D-alanine carboxypeptidase |
| 16 | Hypothetical |
| 17 | LuxR family transcriptional regulator |
| 18 | Hypothetical |
| 19 | AAA family ATPase |
| 20 | Hydrolase |
| 21 | Phage tail protein |

FIG. 5

| No. | ANNOTATION |
|---|---|
| 1 | Phosphonoacetaldehyde hydrolase |
| 2 | GntR-type transcriptional regulator |
| 3 | FAD-dependent oxidoreductase |
| 4 | Phosphonate transporter (PhnD) |
| 5 | Phosphonate transporter (PhnC) |
| 6 | Phosphonate transporter (PhnE) |
| 7 | Possible SARP |
| 8 | Citrate synthase |
| 9 | 2-Methylcitrate dehydratase |
| 10 | Isocitrate dehydrogenase |
| 11 | MFS transporter |
| 12 | Amidohydrolase |
| 13 | NAD-dependent [PnAA] dehydrogenase (PhpC) |
| 14 | 2-Hydroxyethylphosphonate dioxygenase (PhpD) |
| 15 | 3-Phosphoglycerate dehydrogenase (PhpE) |
| 16 | pepM |
| 17 | Phosphonopyruvate decarboxylase (PhpB) |

| No. | ANNOTATION |
|---|---|
| 18 | Nicotinamide mononucleotide adenyltransferase (PhpF) |
| 19 | Phosphoglycerate transferase (PhpG) |
| 20 | Carboxyphosphoenolpyruvate synthase (PhpH) |
| 21 | Carboxyvinyl-carboxyphosphonate phosphorylmutase (PhpI) |
| 22 | Putative phosphonoformaldehyde dehydrogenase (PhpJ) |
| 23 | Long-chain FA CoA-ligase/Methionyl-tRNA synthase? |
| 24 | Peptide formylase |
| 25 | Oligopeptide transporter |
| 26 | Oligopeptide transporter |
| 27 | Oligopeptide transporter |
| 28 | Oligopeptide transporter |
| 29 | ABC transporter |
| 30 | Oxidoreductase/dehydrogenase (myo-inositole) |
| 31 | Siderophore short-chain oxidoreductase |
| 32 | Ornithine/DAP/Arg decarboxylase |
| 33 | Possible amidase or peptidase |

PHOSPHONIC ACID COMPOUNDS AND SCREENING METHOD

RELATED APPLICATION

This application claims priority to U.S. Provisional Patent Application No. 62/027,381 filed on Jul. 22, 2014; the disclosure of which is incorporated by reference herein in its entirety.

STATEMENT REGARDING FEDERALLY SPONSORED RESEARCH OR DEVELOPMENT

This invention was made with government support under contract numbers P01 GM077596 B awarded by the National Institutes of Health. Accordingly, the Federal Government has certain rights to this invention.

FIELD OF THE INVENTION

The present invention relates to pharmaceutical compositions comprising a phosphonic acid compound, such as a natural product. Such compounds can include, such as an antibiotic or compound with other activity, derived from an *Actinobacteria* strain having a gene encoding pepM (phosphoenolpyruvate phosphomutase) or a pepM-dependent biosynthetic pathway. The present invention also relates to methods for treating or preventing or reducing the risk of a bacterial infection by administering a therapeutically effective or prophylactically effective amount of a phosphonic acid antibiotic, or a pharmaceutical composition containing such an antibiotic, to a patient or subject in need thereof. The present invention further relates to methods for isolating, purifying, and identifying such phosphonic acid compounds from *Actinobacteria* strains.

BACKGROUND

The use of genomic data to enable discovery of novel biological processes, often referred to as genome mining, has the potential to revolutionize numerous areas of modern biology. Among these, the field of natural product discovery lies near the top. These biologically-produced small molecules have been the source or inspiration for nearly two-thirds of all human medicines (Reference 1), yet research in this area has dwindled in recent years due to high costs and increasing rates of rediscovery. Within the natural product biosynthesis field, it has been widely suggested that the solution to these problems lies in the use of genome mining (References 2,3). Thus, by focusing research efforts on strains that encode natural product biosynthetic genes with uncharacterized products, one can de-replicate, streamline and accelerate the discovery process. Indeed, genome mining has led to the discovery of several novel natural products (References 2-4). While these successes clearly demonstrate the feasibility of the approach, the studies conducted to date have been limited to individual strains or small collections. If we hope to revitalize the use of natural products in the pharmaceutical industry, genome mining must be realized as a high-throughput discovery process superior to currently used methods. Here, we show the feasibility of this approach in a campaign to identify the full repertoire of phosphonic acid natural products produced by collection of over 10,000 *actinobacteria*.

Phosphonic acid natural products possess a number of traits that make them ideal candidates for large-scale genome mining. First and foremost, phosphonates have great pharmaceutical potential, with a commercialization rate of 15% (3 of 20 isolated compounds) (Reference 5), much higher than the 0.1% average estimated for natural products as a whole (Referenece 6). The potent bioactivity of phosphonates derives from their chemical mimicry of essential metabolites, including phosphate esters and anhydrides, as well as carboxylate reaction intermediates (Reference 5). Given the ubiquitous presence of these chemical moieties in biology, phosphonates are unrivaled in the range of targets they can potentially affect. Consistent with this idea, phosphonates with herbicidal, insecticidal, antibacterial, antiparasitic, antiviral and antihypertensive activities are known. Notable examples include fosfomycin (Monurol®), clinically prescribed for acute cystitis, FR-900098 and fosmidomycin, antimicrobials undergoing clinical trials for malaria, and phosphinothricin, the active component in several commercial herbicides (Liberty®, Basta®, and Rely®). (References 5, 7). Second, the methodology needed for gene-based discovery of phosphonate biosynthetic loci has already been established). This method relies on the fact that all but two characterized phosphonate biosynthetic pathways begin with the enzyme phosphoenolpyruvate mutase, encoded by the pepM gene. Thus, amplification of an internal fragment of the pepM gene with degenerate PCR primers allows identification of strains or plasmid clones that encode phosphonate biosynthetic pathways. Third, gene-based surveys have proven that phosphonate biosynthesis is relatively common in microorganisms, with the greatest diversity of unexplored biosynthetic pathways observed within *Actinobacteria* (Reference 13). Finally, the unique chemical properties of the carbon-phosphorus bond allow direct and unambiguous identification of phosphonates in complex mixtures of metabolites using mass-spectrometry (MS) and nuclear magnetic resonance (NMR) spectroscopy, even when the structure of the molecule in question is unknown (References 14, 15). These detection methods facilitate the purification and characterization of phosphonate natural products, a process that is, at best, extremely laborious for other natural product classes that lack analogous class-specific analytical chemistry assays.

The discovery of natural products, an important source of human medicines, is critical for the development of new therapeutics against health threats including cancer and multi-drug resistant pathogens. Yet in recent years, industrial development of pharmaceuticals from natural products has been stymied due to a variety of reasons, including the repeated discovery of previously known compounds. Here we demonstrate large scale genomics as one potential solution to this problem by mining a collection of 10,000 actinomycetes for novel phosphonic acids, an important class of natural products with antimicrobial, -viral, -malarial, and herbicidal activities. The framework described here provides a foundation for rapid, large-scale discovery of other classes of natural products and their use as lead compounds in the pharmaceutical industry.

BRIEF DESCRIPTION OF THE FIGURES

FIG. 3 depicts putative argolaphos biosynthetic genes within *S. monomycini* B-24309. Annotations are based on BLAST. Core genes encoding for enzymes for aminomethyl phosphonate biosynthesis are Nos. 6-11 (pepM is No. 7). Genes encoding for potential peptide formation enzymes are Nos. 2 and 15 and arginine hydroxylation is No. 5.

FIG. 5 depicts the putative hydrogenphosphinate biosynthetic genes within Nonomuraea B-24552. Annotations are based on BLAST. Core genes encoding for enzymes predicted for phosphinate biosynthesis are Nos. 8-10 and 13-23 (pepM is No. 16). Genes encoding for potential enzymes that modify DMPT are Nos. 25 and 30-33. Genes associated with phosphonate degradation pathways are Nos. 1 and 4-6.

SUMMARY

Figure 1:
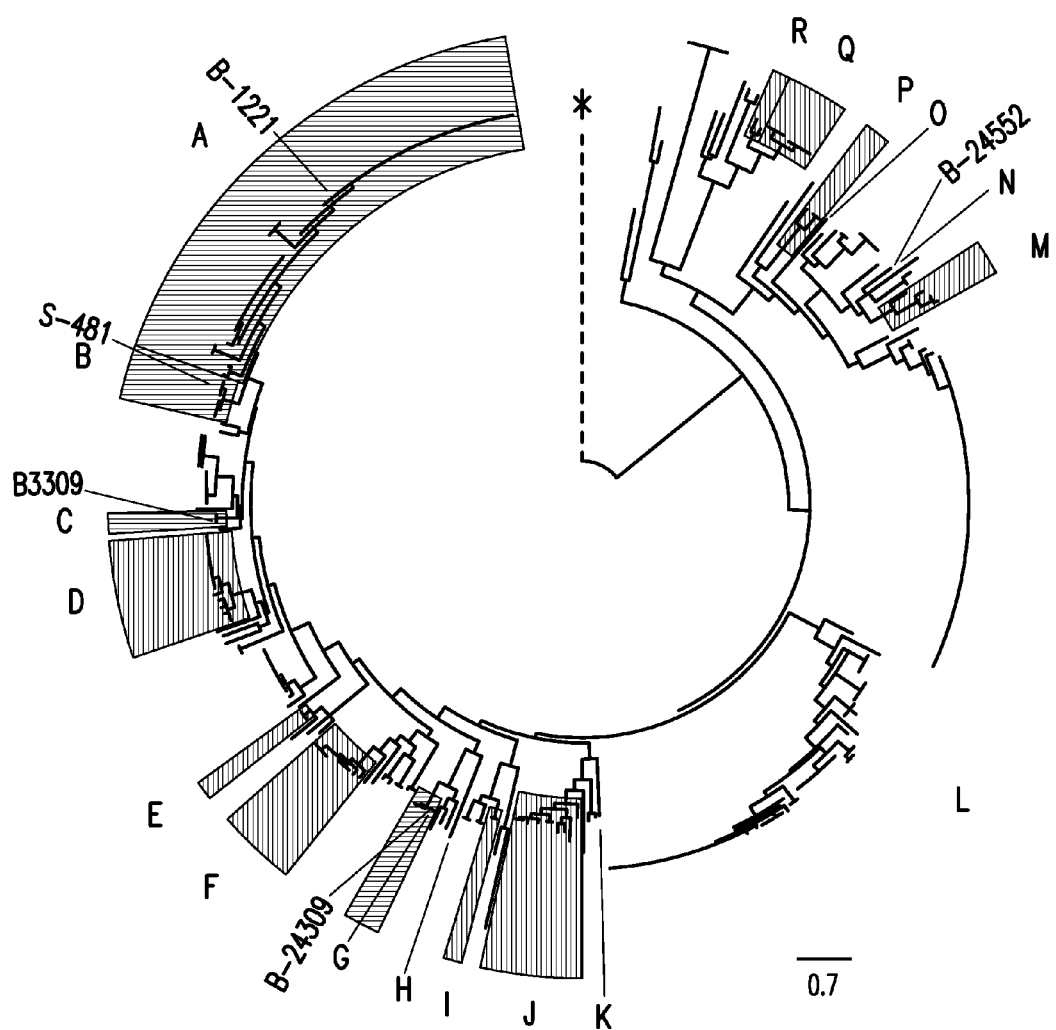
FIG. 1 depicts the phylogeny of actinomycete pepMs with methylisocitrate lyase (dashed line with asterick) as the outgroup. Sequences of strains that produce previously reported PnPs are: actinomycetes (D, E, F, I, J, M, P, Q, and R) and other taxa (H, K, and O) branches, and strains producing PnPs isolated in this study are in (A, B, C, G, and N). Vertical hatching (known PnP) and horizontal hatching (new PnP) denotes clades containing pepM sequences with 80% or higher shared amino acid identity. A—cyanohydroxymethylphosphonate; B—phosphonocystoximate; C—valinophos; D—phosphonothrixin; E—dehydrophos; F—fosfazinomycins; G—argolaphos; H—methylphosphonate derivatives; I—FR-900098; J—plumbemycins and phosacetamycin; K—rhizocticins; L—fosmidomycin; M—phosphinothricin peptides; N—desmethylphosphinothricin; O—fosfomycin (*Pseudomonas*); P—SF-2312; Q—fosfomycin (*Streptomyces*); R—2-hydroxyethylphosphonate polyglycans.

Although natural products have been a particularly rich source of human medicines, the rate at which new molecules are being discovered is declining precipitously. Based on the large number of natural product biosynthetic genes in microbial genomes, many have suggested "genome mining" as an approach to revitalize discovery efforts; however this idea has yet to be demonstrated on a large-scale. To test the feasibility of high-throughput genome mining, we screened a collection of over 10,000 *Actinobacteria* for the genetic potential to make phosphonic acids, a class of natural products with diverse and useful bioactivities. *Actinobacteria* is a phylum of Gram-positive bacteria, generally having a high guanine and cytosine content in their DNA. Within this phylum is the actinomycyte (actinomycetales) order, which is a heterogeneous group of primarily anaerobic Gram-positive bacteria noted for their filamentous and branching growth pattern that can result in a colony or mycelium. Initial characterization of the approximately 280 positive strains allowed identification of previously undescribed natural products, including an unusual thiohydroximate phosphonate and a broad-spectrum phosphonopeptide antibiotic. Among these are argolaphos, a broad spectrum antibacterial phosphonopeptide composed of aminomethylphosphonate in peptide linkage to a rare amino acid $N^5$-hydroxyarginine, valinophos, an N-acetyl L-valine ester of 2,3-dihydroxypropylphosphonate, and phosphonocystoximate, an unusual thiohydroximate-containing molecule representing a new chemotype of sulfur-containing phosphonate natural products. Analysis of the genome sequences from the remaining strains suggests that at the gene level the majority of the phosphonate biosynthetic repertoire of *Actinobacteria* has been captured. This de-replicated strain collection now provides a reservoir of numerous, as yet undiscovered, phosphonate natural products.

Without wishing to be bound by any particular theory, there can be discussion herein of beliefs or understandings of underlying principles or mechanisms relating to embodiments of the disclosure. It is recognized that regardless of the ultimate correctness of any explanation or hypothesis, an embodiment of the disclosure can nonetheless be operative and useful.

The foregoing and other objects and features of the disclosure will become more apparent from the following detailed description, which proceeds with reference to the accompanying figures.

Further embodiments, forms, features, aspects, benefits, objects, and advantages of the present application shall become apparent from the detailed description and figures provided herewith.

DETAILED DESCRIPTION

The present invention relates to a pharmaceutical composition comprising a phosphonic acid compound, such as for example, an antibiotic.

In one aspect the present invention relates to a pharmaceutical composition comprising a phosphonic acid antibiotic, wherein said antibiotic is derived from a bacteria strain of the (taxonomic) phylum *Actinobacteria*.

In another aspect the present invention relates to a pharmaceutical composition, wherein said antibiotic is derived from a bacteria strain of the (taxonomic) order *Actinomycete* (*Actinomycetales*).

In another aspect the present invention relates to a pharmaceutical composition, wherein said antibiotic is derived from a bacteria strain of *Actinobacteria* having a gene encoding pepM (phosphoenolpyruvate phosphomutase) or a pepM-dependent biosynthetic pathway.

In another aspect the present invention relates to a pharmaceutical composition, wherein said antibiotic is derived from a genetically modified bacteria strain of *Actinobacteria*.

In another aspect the present invention relates to a pharmaceutical composition, wherein said antibiotic is derived from a bacteria strain of *Actinobacteria* that produces cyanohydroxymethylphosphate (CyHMPn), plumbemycin, fosfazinomycin, dhydrophos, SF-2312, fosfomycin, or phosphonothrixin, and combinations thereof.

In another aspect the present invention relates to a pharmaceutical composition, wherein said antibiotic is derived from a bacteria strain of *Actinobacteria* selected from the genera *Streptomyces, Saccharothrix, Actinoalloteichus, Micromonospora, Actinoplanes, Dactylosporangium, Glycomyces, Kitasatospora, Nonomuraea, Rhodococcus, Saccharopolyspora, Ampullariella, Amycolata, Atopobium, Catenuloplanes, Frankia, Goodfellowiella, Kibdelosporangium, Kutzneria, Nocardia, Nocardiopsis, Olsenella, Salinospora, Stackebrandtia*, or *Umezawaea*, and combinations thereof.

In another aspect the present invention relates to a pharmaceutical composition, wherein said bacteria strain of *Streptomyces* is selected from *Streptomyces monomycini* NRRL B-24309, *Streptomyces* sp. NRRL S-474, or *Streptomyces* sp. NRRL S-481, and combinations thereof.

In another aspect the present invention relates to a pharmaceutical composition comprising a compound selected from the group consisting of

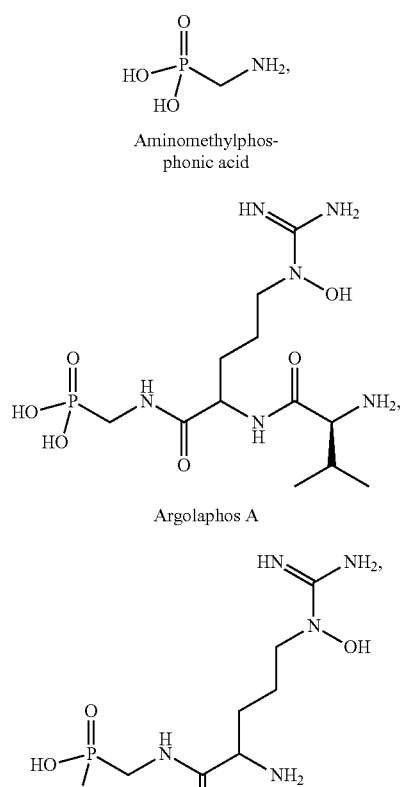

Compound 1
Aminomethylphosphonic acid

Compound 2
Argolaphos A

Compound 3
Argolaphos B

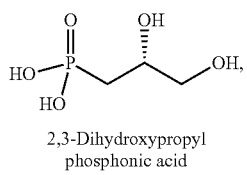

Compound 4
2,3-Dihydroxypropyl phosphonic acid

-continued

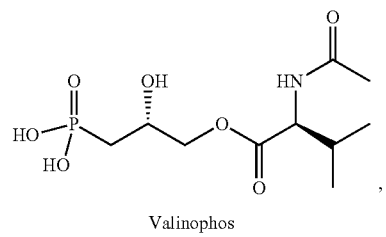

Compound 5
Valinophos

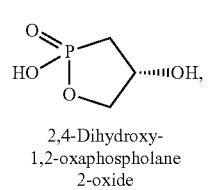

Compound 6
2,4-Dihydroxy-1,2-oxaphospholane 2-oxide

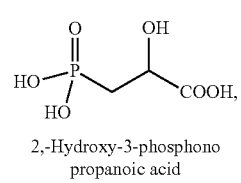

Compound 7
2,-Hydroxy-3-phosphono propanoic acid

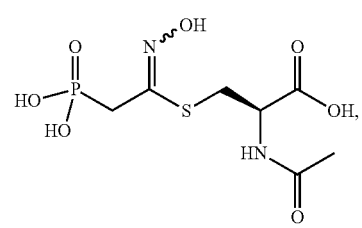

Compound 8
Phosphonocystoximic acid

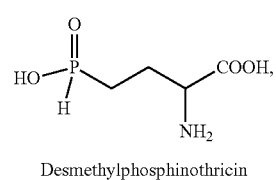

Compound 9
Desmethylphosphinothricin

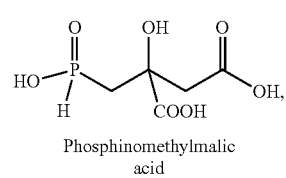

Compound 10
Phosphinomethylmalic acid

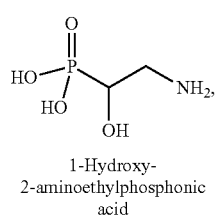

Compound 11
1-Hydroxy-2-aminoethylphosphonic acid

-continued

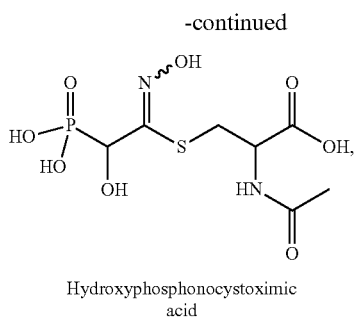

Compound 12

Hydroxyphosphonocystoximic acid

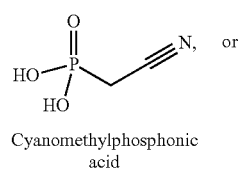

Compound 13

Cyanomethylphosphonic acid

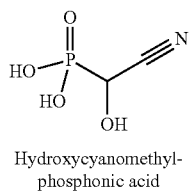

Compound 14

Hydroxycyanomethylphosphonic acid and pharmaceutically acceptable salts, esters, and prodrugs thereof, and mixtures thereof.

In another aspect the present invention relates to a method for treating, preventing, or reducing the risk of a bacterial infection in a subject in need thereof comprising administering a therapeutically effective or prophylactically effective amount of a phosphonic acid antibiotic.

In another aspect the present invention relates to a method, wherein said antibiotic is derived from a bacteria strain of the (taxonomic) phylum *Actinobacteria*.

In another aspect the present invention relates to a method, wherein said antibiotic is derived from a bacteria strain of the (taxonomic) order *Actinomycete (Actinomycetales)*.

In another aspect the present invention relates to a method, wherein said antibiotic is derived from a bacteria strain of *Actinobacteria* having a gene encoding pepM (phosphoenolpyruvate phosphomutase) or a pepM-dependent biosynthetic pathway.

In another aspect the present invention relates to a method, wherein said antibiotic is derived from a genetically modified bacteria strain of *Actinobacteria*.

In another aspect the present invention relates to a method, wherein said antibiotic is derived from a bacteria strain of *Actinobacteria* that produces cyanohydroxymethylphosphate (CyHMPn), plumbemycin, fosfazinomycin, dhydrophos, SF-2312, fosfomycin, or phosphonothrixin, and combinations thereof.

In another aspect the present invention relates to a method, wherein said antibiotic is derived from a bacteria strain of *Actinobacteria* selected from the genera *Streptomyces, Saccharothrix, Actinoalloteichus, Micromonospora, Actinoplanes, Dactylosporangium, Glycomyces, Kitasatospora, Nonomuraea, Rhodococcus, Saccharopolyspora, Ampullariella, Amycolata, Atopobium, Catenuloplanes, Frankia, Goodfellowiella, Kibdelosporangium, Kutzneria, Nocardia, Nocardiopsis, Olsenella, Salinospora, Stackebrandtia,* or *Umezawaea*, and combinations thereof.

In another aspect the present invention relates to a method, wherein said bacteria strain of *Streptomyces* is selected from *Streptomyces monomycini* NRRL B-24309, *Streptomyces* sp. NRRL S-474, or *Streptomyces* sp. NRRL S-481, and combinations thereof.

In another aspect the present invention relates to a method for treating, preventing, or reducing the risk of a bacterial infection in a subject in need thereof comprising administering a therapeutically effective or prophylactically effective amount of a compound selected from the group consisting of

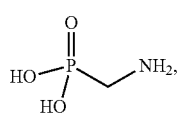

Compound 1

Aminomethylphosphonic acid

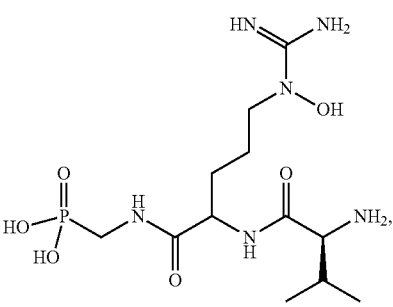

Compound 2

Argolaphos A

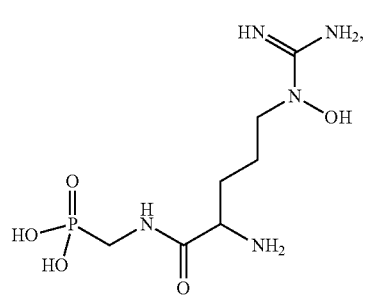

Compound 3

Argolaphos B

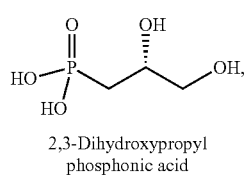

Compound 4

2,3-Dihydroxypropyl phosphonic acid

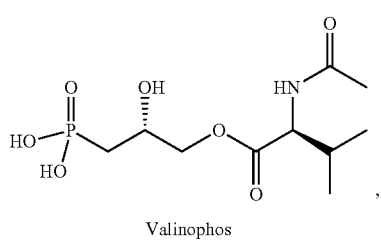

Compound 5

Valinophos

-continued

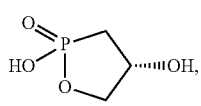

2,4-Dihydroxy-
1,2-oxaphospholane
2-oxide

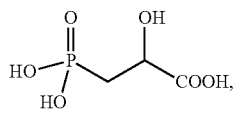

2,-Hydroxy-3-phosphono
propanoic acid

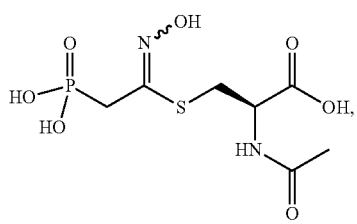

Phosphonocystoximic
acid

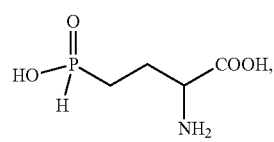

Desmethylphosphinothricin

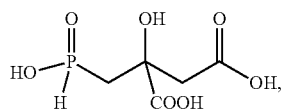

Phosphinomethylmalic
acid

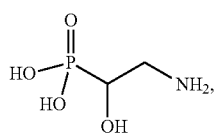

1-Hydroxy-
2-aminoethylphosphonic
acid

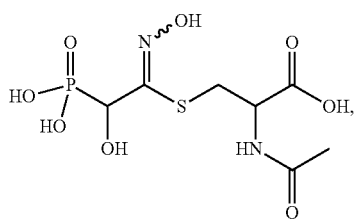

Hydroxyphosphonocystoximic
acid

-continued

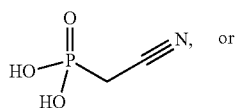

Cyanomethylphosphonic
acid

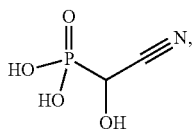

Hydroxycyanomethyl-
phosphonic acid and pharmaceutically acceptable salts, esters, and prodrugs thereof, and mixtures thereof.

In another aspect the present invention relates to the use of a phosphonic acid antibiotic in the manufacture of a medicament for treating, preventing, or reducing the risk of a bacterial infection in a subject in need thereof.

In another aspect the present invention relates to the use of a compound selected from the group consisting of

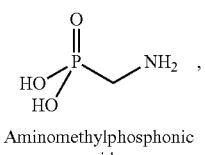

Aminomethylphosphonic
acid

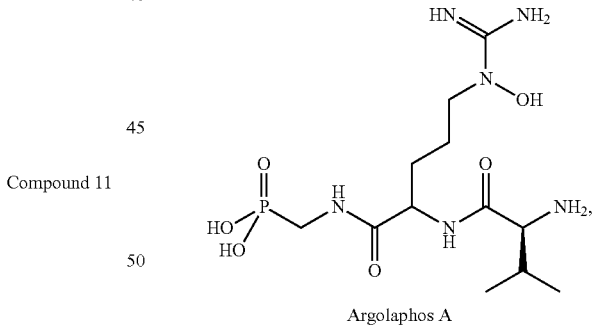

Argolaphos A

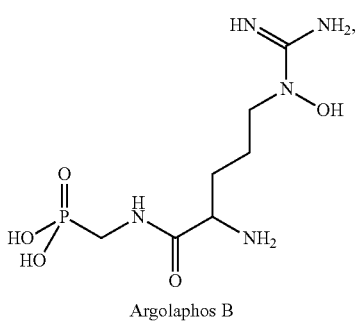

Argolaphos B

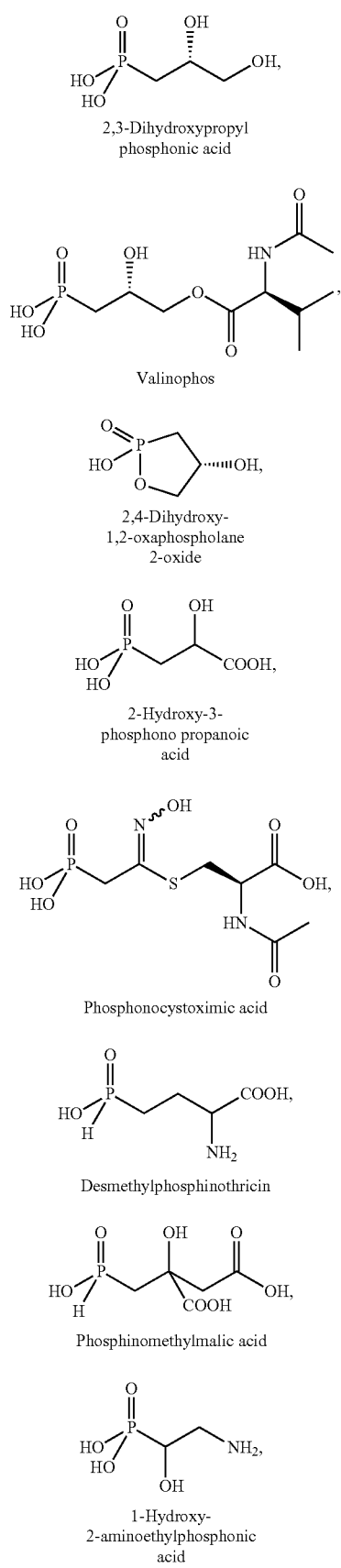

2,3-Dihydroxypropyl phosphonic acid

Valinophos 2,4-Dihydroxy-1,2-oxaphospholane 2-oxide

2-Hydroxy-3-phosphono propanoic acid

Phosphonocystoximic acid

Desmethylphosphinothricin

Phosphinomethylmalic acid

1-Hydroxy-2-aminoethylphosphonic acid

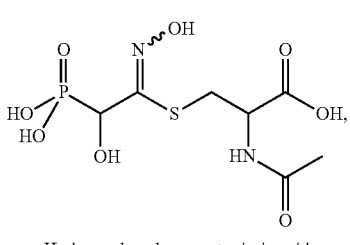

Hydroxyphosphonocystoximic acid

Cyanomethylphosphonic acid

Hydroxycyanomethylphosphonic acid and pharmaceutically acceptable salts, esters, and prodrugs thereof, and mixtures thereof, in the manufacture of a medicament for treating, preventing, or reducing the risk of a bacterial infection in a subject in need thereof.

In another aspect the present invention relates to a compound selected from the group consisting of

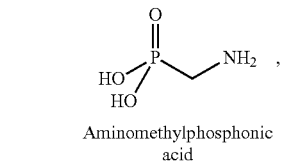

Aminomethylphosphonic acid

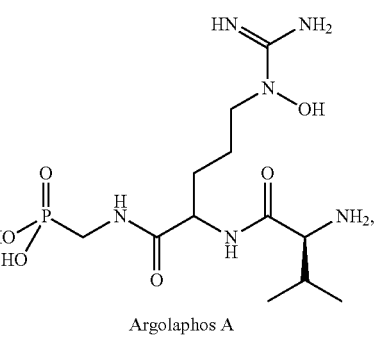

Argolaphos A

-continued

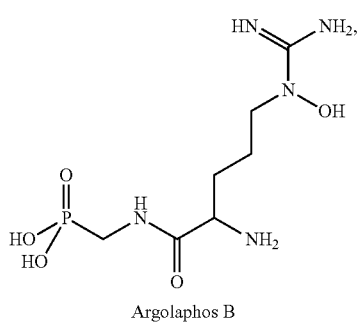

Argolaphos B

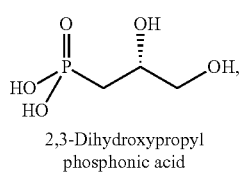

2,3-Dihydroxypropyl phosphonic acid

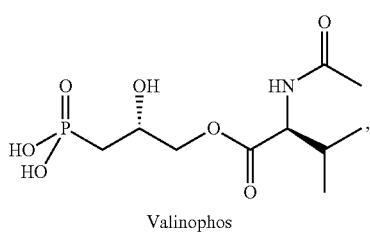

Valinophos

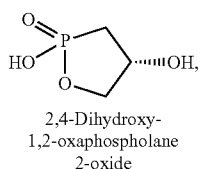

2,4-Dihydroxy-1,2-oxaphospholane 2-oxide

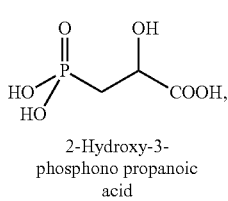

2-Hydroxy-3-phosphono propanoic acid

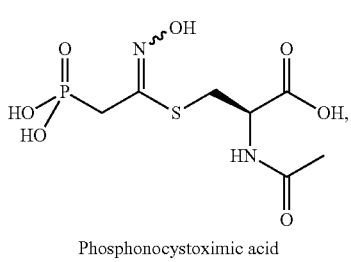

Phosphonocystoximic acid

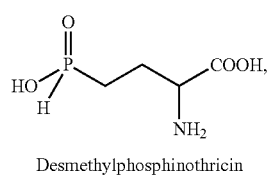

Desmethylphosphinothricin

Compound 3

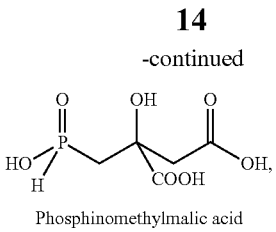

Phosphinomethylmalic acid

Compound 4

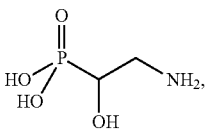

1-Hydroxy-2-aminoethylphosphonic acid

Compound 5

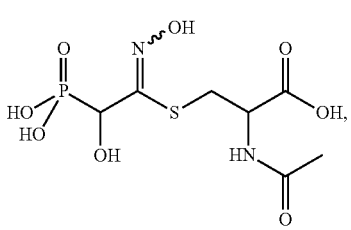

Hydroxyphosphonocystoximic acid

Compound 6

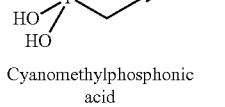

Cyanomethylphosphonic acid

Compound 7

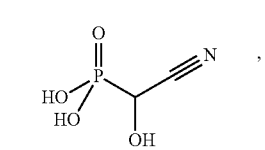

Hydroxycyanomethylphosphonic acid

Compound 8

Compound 9

Compound 10

Compound 11

Compound 12

Compound 13

Compound 14 and pharmaceutically acceptable salts, esters, and prodrugs thereof, and mixtures thereof.

Genome Mining

Rather than look for new molecules directly themselves, it has been found useful to look for organisms with the genetic capacity to produce the molecules, and then find conditions where the molecules are made, purify the compounds, determine their structures, and identify their bioactivities. This process is referred to herein as genome mining.

To identify putative phosphonate-producing microorganisms, we screened a collection of over 10,000 *actinomycetes* for the presence of pepM. The strains examined include ca. 2500 isolated in our laboratory (Reference 13) and nearly 7500 from the ARS Culture Collection (NRRL) at the National Center for Agricultural Utilization Research. This culture collection encompasses species from 117 different genera (Table 1), including important industrial strains and the retired collections of prominent *streptomycete* researchers (Waksman, Gottlieb, Shirling, etc.). See, for example, the ARS (Agriculture Research Service) Culture Collection of the US Department of Agriculture, (also known as the NRRL Collection) website. The Collection is one of the largest public collections of microorganisms in the world, currently containing approximately 99,000 strains of *actino-* mycetes, bacteria, molds, and yeasts. The collection is housed within the Bacterial Foodborne Pathogens and Mycology Research Unit at the National Center for Agricultural Utilization Research in Peoria, Ill. See nal.ncaur.usda.gov.

Initial screening of these strains by $^{31}$P NMR spectroscopy suggested that at least 45 of the 250 strains produced phosphonates. Spent medium from five of these strains exhibited antibacterial activity using a phosphonate-specific bioassay (Reference 8).

TABLE 1

Depicts the Taxonomic Distribution of the
USDA Collection of Acinomycete Strains.*

*Actinoallomurus, Actinoalloteichus, Actinobacillus, Actinocatenispora, Actinocorallia, Actinokineospora, Actinomadura, Actinomonospora, Actinomyces, Actinoplanes, Actinopolymorpha, Actinopolyspora, Actinospica, Actinosporangium, Actinosynnema, Aeromicrobium, Agromyces, Allokutzneria, Amorphosporangium, Ampullariella, Amycolata, Amycolatopsis, Astropsorangium, Blastococcus, Brevibacterium, Catellatospora, Catenirulispora, Catenulispora, Catenuloplanes, Cellulomonas, Cellulosimicrobium, Clavibacter, Corynebacterium, Couchioplanes, Crossiella, Cryptosporangium, Cupolomyces, Curtobacterium, Dactylosporangium, Dermacoccus, Dermatophilus, Dietzia, Faenia, Frankia, Geodermatophilus, Glycomyces, Goodfellowiella, Gordonia, Haloglycomyces, Herbidospora, Humibacillus, Humihabitans, Intrasporangium, Kibdelosporangium, Kineococcus, Kineosporia, Kitasatosproa, Kocuria, Kribbella, Kutzneria, Lechevalieria, Lentzea, Longispora, Marmoricola, Microbacterium, Microbispora, Micrococcus, Microellobosporia, Micropolyspora, Microterricola, Microtetraspora, Millisia, Mycetocola, Mycobcterium, Mycoplana, Nocardioides, Nocardiopsis, Nonomuraea, Norcardioides, Oeskovia, Oryzihumus, Patulibacter, Phycicoccus, Pilimelia, Planobispora, Planomonospora, Prausella, Promicromonospora, Pseudoamycolata, Pseudonarcia, Rhodococcus, Rothia, Saccharomonospora, Saccharopolyspora, Saccharothrix, Salana, Salinispora, Sphaerisporangium, Spirillospora, Sporichthya, Stackebrantia, Streptacidiphilus, Streptoalloteichus, Streptosporangium, Streptoverticillium, Thermoactinopolyspora, Thermobifida, Thermomonospora, Thermopolyspora, Tsukamurella, Umezawaea, Vemicosispora, Williamsia,* and Unidentified Acinomycete.

*Streptomyces (87%), thermoactinomyces (1%), norcardia (2%), micromonospora (4%), other genera (<1% each).

To enable rapid screening, genomic DNA was isolated from all strains and arrayed into a 96-well format. Blind PCR screening of this library identified 403 putative phosphonate producers (Reference 16). Subsequent draft genome sequencing of all candidate strains confirmed the presence of pepM in 278 strains, including 244 from the NRRL collection, 30 from our laboratory collection, and four additional strains specifically added to the study because of their known ability to produce phosphonothrixin (Reference 17), SF-2312 (Reference 18), FR-900098 (Reference 19) and fosmidomycin (Reference 20). The majority (87%) of the pepM strains are *Streptomyces*, with the remainder scattered among 24 genera, a distribution that mirrors the composition of the strain collection (Table 2).

TABLE 2

Taxonomic Distribution of all pepM+ actinomycetes (311).

*Streptomyces* (270)*, *Saccharothrix* (7), *Actinoalloteichus* (3), *Micromonospora* (3), *Actinoplanes* (2), *Dactylosporangium* (2), *Glycomyces* (2), *Kitasatospora* (2), *Nonomuraea* (2), *Rhodococcus* (2), *Saccharopolyspora* (2), *Ampullariella* (1), *Amycolata* (1), *Atopobium* (1), *Catenuloplanes* (1), *Frankia* (1), *Goodfellowiella* (1), *Kibdelosporangium* (1), *Kutzneria* (1), *Nocardia* (1), *Nocardiopsis* (1), *Olsenella* (1), *Salinospora* (1), *Stackebrandtia* (1), and *Umezawaea* (1)

*Values within parentheses indicate the number of strains classified for each genus. Note 311 strains of actinomycetes in total.

A single copy of pepM was found in most strains, with the exception of five strains, each of which encodes two distinct pepM homologs. Significantly, all known phosphonate producers deposited in the NRRL collection, including producers of fosfomycin, dehydrophos, and phosalacine, were rediscovered in our blind screening approach, validating the sensitivity and thoroughness of our pepM-based screen.

Figure 2:
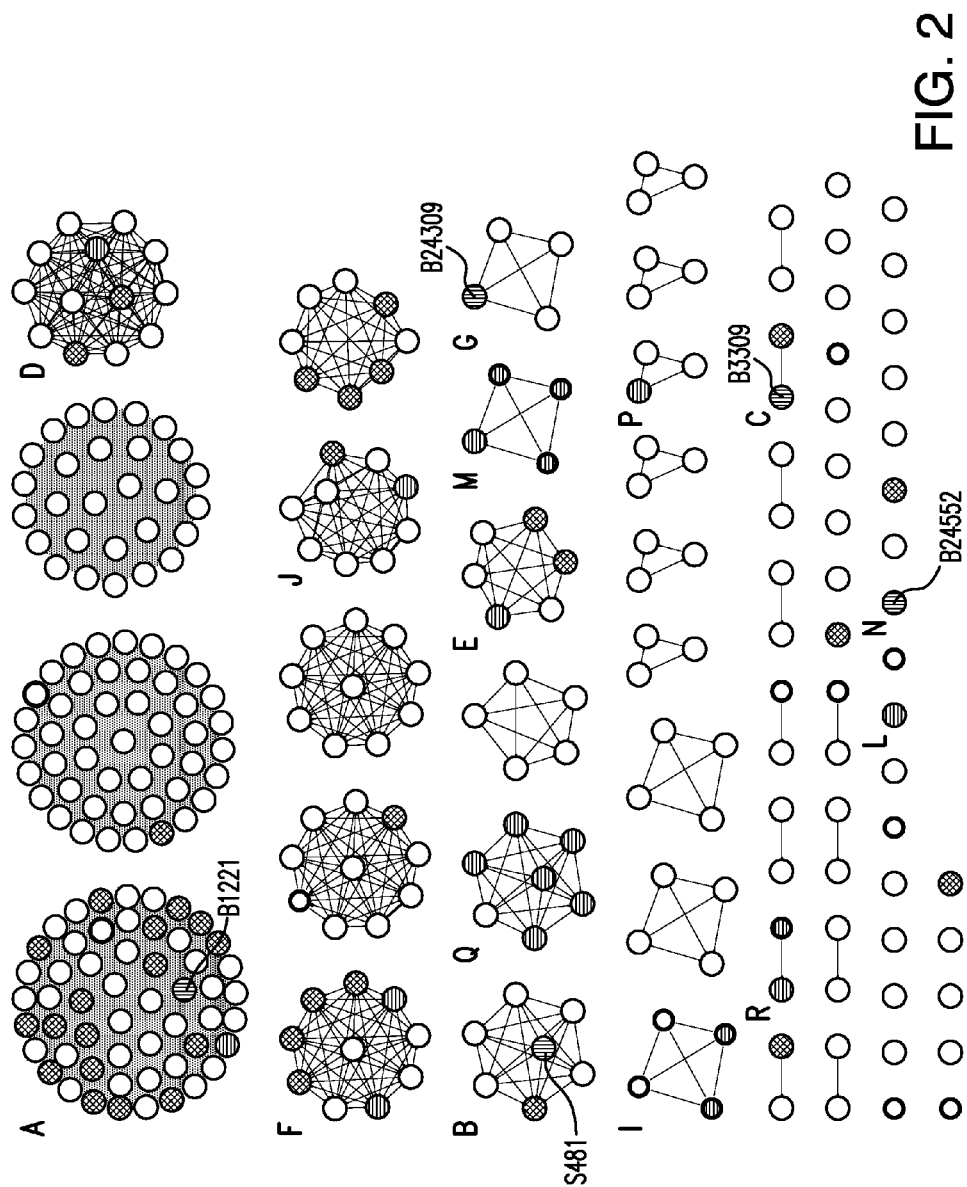
FIG. 2 depicts a network of putative PnP gene-clusters within actinomycetes. Each node in the network represents one gene cluster and edges are based on automated scoring and manual curation. Nodes with heavy black outlines are sequences obtained from publicly available genomes. Horizontal hatching indicates known producers of previously reported PnPs, Diagonal criss-cross hatching indicates unknown PnPs detected in $^{31}$P-NMR screening, and vertical hatching indicates new PnPs described here. A—cyanohydroxymethylphosphonate; B—phosphonocystoximate; C—valinophos; D—phosphonothrixin; E—dehydrophos; F—fosfazinomycins; G—argolaphos; I—FR-900098; J—plumbemycins and phosacetamycin; L—fosmidomycin; M—phosphinothricin peptides; N—desmethylphosphinothricin; P—SF-2312; Q—fosfomycin (*Streptomyces*); R—2-hydroxyethylphosphonate polyglycans.

De-replication of phosphonate biosynthetic pathways and production screening: Although recent years have seen great improvements in subtractive MS- and NMR-based screening methods for new natural products (References 48, 49), in our hands, $^{31}$P NMR spectroscopy has proven more reliable than MS-based methods for detection of phosphonates of unknown structure. However, NMR screening of 10,000 strains is impractical. The genomic data were used to de-replicate the candidate strains prior to purification and characterization of the natural products they produced. To do this, we employed two established methods for linking genetic data to phosphonate natural product diversity (Reference 13). Initially, we examined the relatedness of the pepM proteins encoded by the 278 strains, revealing 168 unique sequences, distributed among 78 groups at the 80% sequence identity level (FIG. 1). Because natural product biosynthetic genes are almost always clustered together in a single chromosomal locus, we also examined the similarity of the genes surrounding pepM. This parallel gene neighborhood approach produced 64 discrete groups (gene neighborhoods) (FIG. 2). Known phosphonate producers map to ten of these groups, most of which also include additional strains. Thus, our genome mining effort revealed 55 new potential producers of cyanohydroxymethylphosphonate (CyHMPn), 8 of plumbemycin, 7 of fosfazinomycin, 2 of dehydrophos, 2 of SF-2312, and 1 of fosfomycin. Production of the predicted molecule was validated for several of these strains using high-resolution mass spectrometry (HRMS). We also identified the putative biosynthetic gene cluster for phosphonothrixin in the genome sequence of the only known producer, Saccharothrix ST-888 (Reference 17). Our observation of phosphonothrixin in the spent media of four of the thirteen strains that carry this gene cluster, provides strong evidence that these genes direct the synthesis of this herbicidal compound. After elimination of the strains linked to known products, we were left with a de-replicated collection of 192 strains grouped into 69 pepM clades and 55 pepM gene cluster families. Three of these, *S. monomycini* NRRL B-24309, *Streptomyces* sp. NRRL S-474 and *Streptomyces* sp. NRRL S-481, were of particular interest because they elicited positive responses in the phosphonate-specific bioassay described above. By both measures of diversity, greater than 85% of the pathways reported here direct synthesis of new posphonate natural products.

Production screening of all 244 pepM$^+$ strains from NRRL by $^{31}$P NMR spectroscopy suggested that at least 45 produced phosphonates. Three of these, *S. monomycini* NRRL B-24309, *Streptomyces* sp. NRRL S-474 and *Streptomyces* sp. NRRL S-481, were of particular interest because they elicited positive responses in a phosphonate-specific bioassay (Reference 8) and because the genomic information illustrated that their biosynthetic gene clusters were novel.

Figure 6:
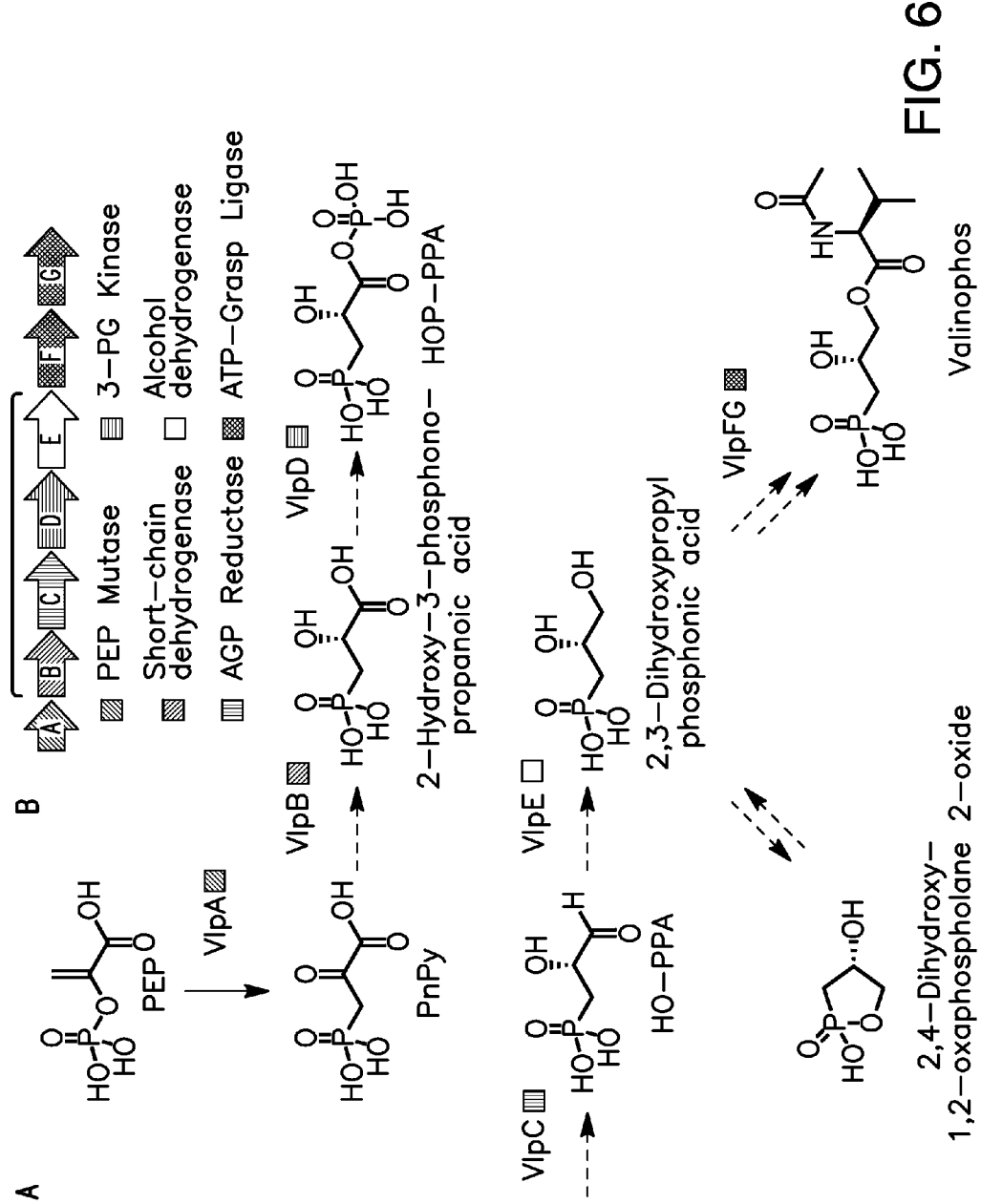
FIG. 6 depicts schemes for *S. durhamensis* B-3309, where part A depicts isolated compounds and a proposed pathway for valinophos biosynthesis and part B depicts a putative valinophos (Vlp) gene cluster, with the genetic cassette conserved in phosphonothrixin biosynthesis indicated by brackets.

Two phosphonopeptides, which we have designated argolaphos A and B, were purified from spent media of *S. monomycini* NRRL B-24309. Argolaphos B is comprised of aminomethylphosphonate (AmPn) in peptide linkage with the rare amino acid N$^5$-L-hydroxyarginine (N5-OH-Arg), while argolaphos A has an additional peptide linkage to L-valine (FIG. 3). Although AmPn is not a known natural product, it has been reported as an off-pathway metabolite in mutants blocked for phosphinothricin production (References 21 and 50). N$^5$-Hydroxyarginine has previously been isolated as a free amino acid from strains of *Bacillus cereus* (References 22, 23) and the fungus *Nanniizia gypsea* (*Arthroderma gypseum*) (Reference 24). The pepM gene cluster of *S. monomycini* NRRL B-24309 is fully consistent with this structure, including readily identifiable candidate genes for the synthesis of AmPn, hydroxylation of arginine and peptide bond synthesis (FIG. 6). The pepM gene cluster of *S. monomycini* NRRL B-24309 suggests (FIG. 2B) the AmPn core is synthesized from PEP by homologs of PhpA-E from phosphinothricin biosynthesis (Reference 21).

Argolaphos has broad-spectrum antibacterial activity, with the highest efficacy against *Salmonella typhimurium*, *Escherichia coli*, and *Staphylococcus aureus*, and is weakly inhibitory against *Mycobacterium smegmatis*. Because AmPn and N$^5$-hydroxyarginine are inhibitors with different modes of action (References 22 and 25), the combination of both in argolaphos may serve to enhance its bioactivity. Moreover, it is clear that both moieties contribute to toxicity, because argolaphos is a more potent antibiotic than free AmPn in *E. coli* strains expressing a broad specificity phosphonate transport system. It should be noted that *E. coli* does not synthesize B$_{12}$, nor does it require the vitamin for growth, thus the mechanism of argolaphos activity is likely to be more complex than is suggested by the known bioactivities of free AmPn and N$^5$-L-hydroxyarginine.

Phosphonocystoximates: Two other bioactive strains, *Streptomyces* sp. NRRL S-474 and NRRL S-481, belong to a group of seven strains with a pepM gene cluster similar, but not identical, to the one found in *Streptomyces regensis* NRRL WC-3744, the known producer of CyHMPn (Reference 26). In preliminary experiments, both strains produced several compounds with $^{31}$P NMR signals in the range consistent with phosphonic acids. Only one of these compounds was made in sufficient amounts to allow purification and structural characterization. This molecule, designated phosphonocystoximate, purified by $^{31}$P NMR-guided fractionation of spent media of *Streptomyces* sp. NRRL S-481, represents a new class of sulfur-containing phosphonate natural products (FIG. 3). The S-alkyl thiohydroximate and N-acetyl-cysteine moieties of phosphonocystoximate are chemically similar to biosynthetic intermediates of glucosinolates, natural products with potential antioxidant and anticancer properties, most commonly known as the molecules responsible for the pungent taste of broccoli, Brussels sprouts, and wasabi (Reference 27). Unfortunately, neither of the two strains produced sufficient levels of phosphonocystoximate to allow bioactivity testing of the purified molecule. Thus, the identity of the bioactive phosphonate produced by these strains remains to be determined.

Figure 4:
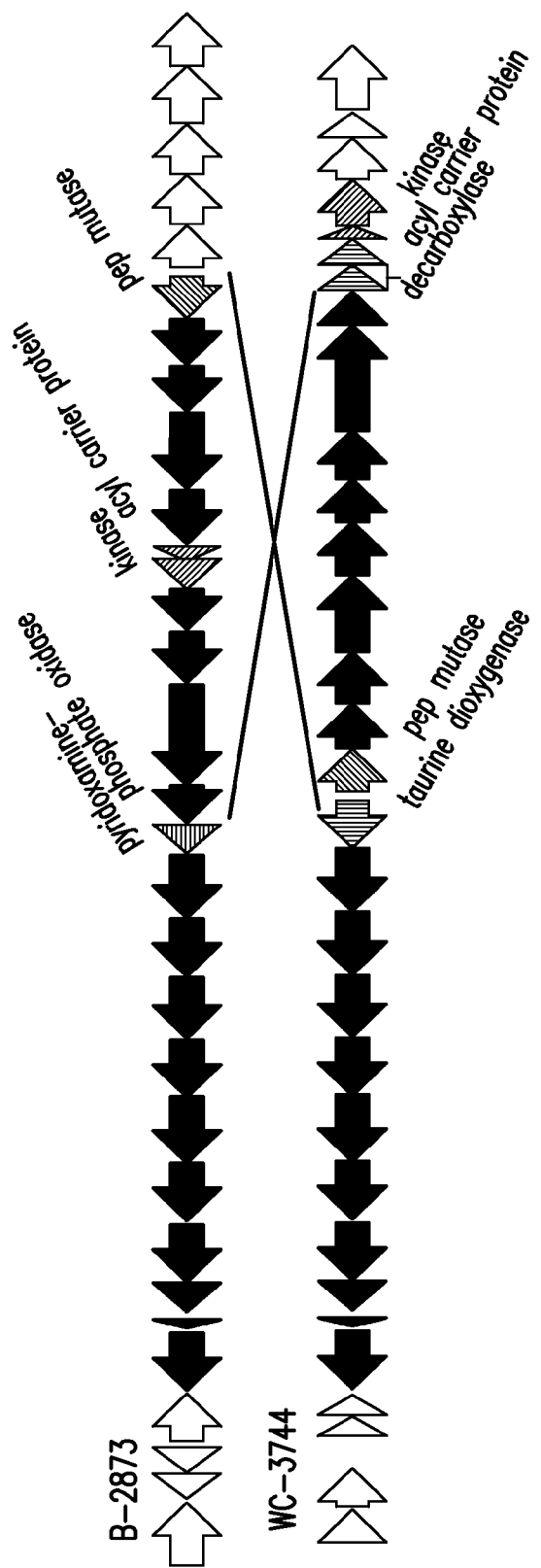
FIG. 4 depicts comparisons between the putative phosphonocystoximate (top) and cyanohydroxymethylphosphonate (bottom) gene clusters. The majority of genes are shared between the two pathways with some notable differences. Genes encoding an α-ketoglutarate dependent dioxygenase (taurine dioxygenase) and phosphonopyruvate decarboxylase are absent from the phosphonocystoximate gene cluster, which instead contains a pyridoxamine-phosphate oxidase homolog. Half of the putative genes for cyanohydroxymethylphosphonate biosynthesis are inverted relative to the same genes for phosphonocystoximate.

Comparisons between the phosphonocystoximate and cyanohydroxymethylphosphonate biosynthetic gene clusters share all but three genes (FIG. 4). The phosphonocystoximate gene cluster lacks homologs of the genes encoding phosphonopyruvate decarboxylase or homocitrate synthase, which are required to drive the thermodynamically unfavorable pepM reaction in other phosphonate biosynthetic pathways (Reference 7). Thus, some of the differences between the gene clusters can be attributed to differences in the enzymatic steps involved in the synthesis of the likely early intermediate 2-aminoethyl phosphonate (2AEPn). This finding also suggests that phosphonocystoximate synthesis involves a novel thermodynamic driving reaction. A second difference lies in the presence of an α-ketoglutarate dependent dioxygenase within the hydroxynitrililpahos gene cluster, which suggested that strains containing the two groups of gene clusters might produce molecules differing by hydroxylation. To test this, we examined spent media from several strains in both groups using HRMS. Strains encoding the related gene cluster families produce a suite of molecules that differ solely by hydroxylation at the α-carbon, relative to the phosphonate moiety. Among these molecules are several unprecedented natural products, including the 1-hydroxy-2-aminoethylphosphonate (1H2AEPn) and hydroxyphosphonocystoximate made by strains encoding the dioxygenase, and nitrilaphos (cyanomethylphosphonate), made by strains lacking this gene. 1H2AEPn was an effective antibiotic against *E. coli* upon induction of phosphonate uptake machinery.

Based on these data, we present a model where 2-aminoethylphosphonate (2AEPn) serves as the common biosynthetic intermediate for both pathways. Consistent with the metabolism of glucosinolates in plants, phosphonocystoximates may be biosynthetic intermediates en route to the formation of a yet unidentified phosphonosinolate. The presence of mycothiol-dependent peptidase and transferase genes suggest mycothiol as the probable source of N-acetylcysteine in phosphonocystoximate formation, similar to the use of glutathione as the source of cysteine in glucosinolates from plants (Reference 27). The FAD-NAD(P)H dependent N-hydroxylase gene within both clusters may oxidize the amine to the oxime. Mycothiol-dependent transferase and peptidase genes suggest mycothiol as the probable source of N-acetylcysteine in phosphonocystoximate formation, similar to the use of glutathione as the source of cysteine in glucosinolates from plants (Reference 27). Accordingly, inositolglucosamine conjugants of phosphonocystoximate and hydroxyphosphonocystoximate were detected from extracts. Subsequent hydrolysis of the peptide bond of the conjugated mycothiol by the encoded peptidases would release the observed phosphonocystoximates. Consistent with the metabolism of glucosinolates in plants, these may be biosynthetic intermediates en route to the formation of a yet unidentified phosphonosinolate. Whether the cyanomethylphosphonates produced by these strains are biosynthetic intermediates or the products of degradation remains to be determined.

Two additional groups of strains were selected for further characterization on the basis of unusual content of their pepM gene neighborhoods. *Streptomyces durhamensis* NRRL B-3309 was selected for further analysis because, like the phosphonocystoximate cluster, it does not encode a known example of an enzyme that could be coupled with pepM to drive the thermodynamically unfavorable rearrangement of PEP to phosphonopyruvate. Two novel phosphonate natural products, 2-hydroxy-3-phosphonopropanoic acid and (R)-2,3-dihydroxypropylphosphonic acid (DH-PPA), and its cyclic ester were purified from spent media after cultivation of this strain. These compounds are likely early intermediates in the formation of a fourth new phosphonate that we name valinophos: an N-acetyl L-valine ester of DHPPA that was also produced by *S. durhamensis* (FIG. 6). Only DHPPA was purified in sufficient quantity to assess bioactivity, which slightly inhibited growth of *Mycobacterium smegmatis*. We contemplate synthetic means to investigate the possibility that antibiotic activity can be enhanced by incorporating DHPPA into peptides as observed for other phosphonates (Reference 5).

We propose a biosynthetic pathway for valinophos that is supported by the content of the pepM gene cluster and the predicted biochemistry of the encoded proteins. Like the phosphonocystoximate cluster, a known example of an enzyme that could be coupled with PEP mutase (V1pA) to drive the thermodynamically unfavorable rearrangement of PEP to PnPy is absent. Instead, V1pB, a putative short-chain dehydrogenase, may reduce PnPy to 2-hydroxy-3-phosphonopropanoic acid (phosphonolactate) in a reaction analogous to the highly favorable reduction of pyruvate to lactate by NADH-dependent lactate dehydrogenases ($K_{eq}=1\times10^5$) (Reference 51). Analogous to the proposed formation of 1-oxo-2-phosphorylethylphosphonic acid by the phosphoglycerate kinase DhpB in dehydrophos biosynthesis (Reference 36), phosphorylation of phosphonolactate by V1pD would yield 2-hydroxy-3-oxo-3-phosphoxypropylphosphonic acid (HOP-PPA). Reduction by V1pC (homologous to N-acetyl γ-glutamyl phosphate reductase) results in 2-hydroxy-3-oxopropylphosphonic acid (HO-PPA) that could be converted to DHPPA via another reduction by V1pE (alcohol dehydrogenase). Although ATP-grasp ligases typically adjoin substrates by amide linkages, these enzymes have also been shown to form ester bonds (Reference 52). Here, ATP-grasp ligases V1pF and G are proposed to install and acetylate L-valine onto DHPPA to yield valinophos. Interestingly, vlpBCDE appears as a conserved cassette within the pepM gene clusters for phosphonothrixin. This observation suggests the early steps for valinophos are the archetype of a new branch of phosphonate biosynthetic pathways, from which phosphonothrixin also originates.

A dedicated pathway for H-phosphinate biosynthesis: *Nonomureae* sp. NRRL B-24552 was chosen for study due to the similarity of its pepM gene cluster to that involved in the synthesis of phosphinothricin tripeptide (PTT), the only known phosphinate natural product. However, unlike the well-characterized PTT biosynthetic gene clusters, *Nonomureae* sp. NRRL B-24552 lacks the genes needed for synthesis of the C—P—C moiety of phosphinothricin (phpK; P-methylase) (FIG. 5), suggesting that this organism may instead produce an H-phosphinate (H—C—P bond motif). Consistent with this idea, we purified 2-phosphinomethylmalic acid and desmethylphosphinothricin (DMPT) from extracts of this strain. DMPT is not a known natural product; however, it has been observed only as a by-product in *S. hygroscopicus* strains with mutations in the PTT pathway (Reference 28). Based on the content of the *Nonomureae* sp. NRRL B-24552 pepM gene cluster and the results of $^{31}$P NMR analyses of spent media, it is likely DMPT is further modified to produce additional H-phosphinates in this organism.

Our successful campaign for phosphonate natural products validates the utility of large-scale genome mining for discovery of new natural products, fulfilling the promise of genomics-enabled drug discovery made 20 years earlier. Including eight molecules we have recently reported elsewhere (References 14, 26, 29), our genome mining strategy has to date yielded 19 new phosphonate natural products. In addition to increasing the number of *acrtinomuycete* phosphonate gene cluster groups by over 8-fold, we have doubled the total diversity of phosphonate pathways identified to date. Moreover, rarefaction and extrapolation analyses suggest that the majority of the remaining phosphonate biosynthetic repertoire of *Actinobacteria* can be found within the de-replicated strain collection (FIG. S14). Accordingly, using our previously published approach (Reference 30), we predict that *Actinobacteria* have a total capacity for ca. 125 distinct pathways for phosphonic acid natural products. The genome-mining of 10,000 strains reported here has already identified strains encoding ca. 78 discrete biosynthetic gene clusters, with multiple producing organisms available for most groups. Lastly, we note that the actinobacterial DNA library and hundreds of genome sequences produced here will inform and enable rapid, large-scale genome-mining for other natural product classes (Reference 30).

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

The disclosure may be further understood by the following non-limiting examples. All references cited herein are hereby incorporated by reference to the extent not inconsistent with the disclosure herewith. Although the description herein contains many specificities, these should not be construed as limiting the scope of the disclosure but as merely providing illustrations of some of the presently preferred embodiments of the disclosure. For example, thus the scope of the disclosure should be determined by the appended aspects and their equivalents, rather than by the examples given.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this disclosure for a given application. In specific applications, the selection of a given anion or cation for preparation of a salt may result in increased or decreased solubility of that salt.

Every formulation or combination of components described or exemplified herein can be used to practice the disclosure, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to Applicant's disclosure, including compounds for which an enabling disclosure is provided in the references cited herein, are not intended to be included in the composition of matter aspects herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Further-more, the advantages described above are not necessarily the only advantages of the disclosure, and it is not necessarily expected that all of the described advantages will be achieved with every embodiment of the disclosure.

All percentages and ratios used herein, unless otherwise indicated, are by weight.

Definitions

A coding sequence is the part of a gene or cDNA which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

Downstream refers to a relative position in DNA or RNA and is the region towards the 3' end of a strand.

Expression refers to the transcription of a gene into structural RNA (rRNA, tRNA) or messenger RNA (mRNA) and subsequent translation of an mRNA into a protein.

An amino acid sequence that is functionally equivalent to a specifically exemplified TCR sequence is an amino acid sequence that has been modified by single or multiple amino acid substitutions, by addition and/or deletion of amino acids, or where one or more amino acids have been chemically modified, but which nevertheless retains the binding specificity and high affinity binding activity of a cell-bound or a soluble TCR protein of the present disclosure. Functionally equivalent nucleotide sequences are those that encode polypeptides having substantially the same biological activity as a specifically exemplified cell-bound or soluble TCR protein. In the context of the present disclosure, a soluble TCR protein lacks the portions of a native cell-bound TCR and is stable in solution (i.e., it does not generally aggregate in solution when handled as described herein and under standard conditions for protein solutions).

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

Isolated means altered by the hand of man from the natural state. If an "isolated" composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'-5'-phosphodiester bonds.

Two DNA sequences are operably linked if the nature of the linkage does not interfere with the ability of the sequences to affect their normal functions relative to each other. For instance, a promoter region would be operably linked to a coding sequence if the promoter were capable of effecting transcription of that coding sequence.

A polypeptide is a linear polymer of amino acids that are linked by peptide bonds.

Promoter means a cis-acting DNA sequence, generally 80-120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into at least one cloning site).

Transformation means the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

As used herein, the terms "patient" or "subject", refers to a human or animal [in the case of an animal, more typically a mammal such as domesticated mammals (e.g., dogs, cats, cattle, sheep, pigs), or animals such as poultry animals and fish and other seafood or freshwater food creatures], that would be subjected to the treatments and compositions of the present invention. Such patient or subject would be considered to be in need of the compounds or pharmaceutical compositions of the present invention or of the methods of treating, preventing, or reducing the risk of a bacterial infection.

As used herein, the term "therapeutically effective amount" refers to an amount of a compound of the present invention (i.e. a pharmaceutical active compound), or a combination of compounds, or an amount of pharmaceutical active compound delivered from a pharmaceutical composition, when administered alone or in combination, to treat, prevent, or reduce the risk of a disease state or condition, for example a bacterial infection. The term also refers to an amount of a pharmaceutical composition containing an active compound or combination of compounds. For example, an effective amount refers to an amount of the compound or an amount of the compound delivered by a pharmaceutical composition given to a recipient patient or subject sufficient to elicit biological activity, for example, activity for treating or preventing a bacterial infection.

As used herein, the phrase "pharmaceutically acceptable" refers to those active compounds, materials, pharmaceutical compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

As used herein, the term "treating" refers to providing a therapeutic intervention to cure or ameliorate a bacterial infection.

As used herein, the term "preventing", refers to completely or almost completely stopping a bacterial infection from occurring, for example when the patient or subject is predisposed to a bacterial infection or at risk of contracting a bacterial infection. Preventing can also include inhibiting, i.e. arresting the development, of a bacterial infection.

As used herein, the term "reducing the risk of", refers to lowering the likelihood or probability of a bacterial infection from occurring, for example when the patient or subject is predisposed to a bacterial infection or at risk of contracting a bacterial infection.

Pharmaceutical Dosage Forms

The following formulations illustrate representative pharmaceutical dosage forms that may be used for the therapeutic or prophylactic administration of a compound of a formula described herein, a compound specifically disclosed herein (for example Compound 1 to 14), or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

EXAMPLES

Media

All formulations are for 1 L of media with components dissolved in deionized (dI) water. Difco granulated agar (Becton, Dickson and Company) was added (16 g/L) prior to sterilization for plates. All other components were of the highest purity commercially available from Sigma-Aldrich or Fisher Scientific.

ATCC172: Soluble starch (20 g), glucose (10 g), yeast extract (5 g), N—Z amine type A (5 g), CaCO$_3$ (1 g); pH was adjusted to 7.3 prior to sterilization.

ISP4: Soluble starch (10 g), K$_2$HPO$_4$ (1 g), MgSO$_4$-7H$_2$O (1 g), NaCl (1 g), (NH$_4$)$_2$SO$_4$ (2 g), CaCO$_3$ (2 g), FeSO$_4$-7H$_2$O (1 mg), ZnSO$_4$-7H$_2$O (1 mg), MnCl$_2$-2H$_2$O (1 mg).

R2AS: Bacto yeast extract (0.5 g), Bacto peptone (0.5 g), Bacto Casamino acids (0.5 g), glucose (0.5 g), potato starch (0.5 g), sodium pyruvate (0.3 g), KH$_2$PO$_4$ (0.3 g), MgSO$_4$-7H$_2$O (0.05 g). pH was adjusted to 7.2 prior to sterilization. Sodium succinate was added to 40 mM afterwards from a 1 M filter-sterilized stock solution. Balch's vitamins (Reference 31) (10 mL) were added after sterilization.

GUBC: Sucrose (10 g), dessicated beef extract (5 g), Casamino acids (5 g), glycerol (5 g), 1 M Na$_2$HPO$_4$—KH$_2$PO$_4$ buffer pH 7.3 (5 mL), Hunter's concentrated base (Reference 32) (2 mL). Balch's vitamins (Reference 31) (10 mL) were added after sterilization.

M9-glucose: Na$_2$HPO$_4$-7H$_2$O (12.8 g), KH$_2$PO$_4$ (3 g), NH$_4$Cl (1 g), NaCl (0.5 g). Glucose (20 mL), MgSO$_4$ (2 mL), and CaCl$_2$ (100 μL) were added from 1 M filter-sterilized stock solutions after autoclaving.

Construction of the *Actinomycete* DNA Library

Each strain from the USDA-Agricultural Research Service actinobacteria collection was revived from lyophilized vials or slants by inoculating into 150 mm×18 mm test tubes containing 5 mL of 172 medium. Liquid cultures were grown at 30° C. on an angled roller drum (75 rpm) for six days and then arrayed by aliquoting (2 mL) into 96-well deep blocks. Supernatants were removed after centrifugation and the remaining cell pellets frozen at −80° C. for 24 hours. Cell pellets were then allowed to completely thaw at room temperature, immediately re-frozen and stored at −20° C.

DNA isolated using the UltraClean-HTP 96-well Microbial DNA Kit (MoBio, Carlsbad, Calif.) according to manufacturer instructions but with the following modifications. Cell pellets were thawed, re-resuspended with 300 μL of MicroBead solution containing lysozyme (1 mg/mL) and DNase-free RNase A (100 μg/mL), and incubated at 30° C. for 1 hour with gentle rocking. Treated cells were then transferred into the 96-well bead plate. After addition of solution MD1, 96-well blocks were firmly sealed with the provided silicon covers, inverted several times to mix, pulsed in a tabletop centrifuge to draw all liquid to the bottom, and incubated in a 70° C. water bath for 20 min. After cooling to room temperature, blocks were attached onto a Restech bead mill and cells lysed by running at setting 20 for 5 min. Blocks were removed, re-oriented so that the side closest to the machine body is now furthest away, and shaken again at setting 20 for an additional 5 min. Prior to DNA elution, spin plates were centrifuged twice to remove residual ethanol and air dried for 20 min at room temperature. DNA was eluted from spin plates by adding 120 μL of pre-heated sterile water (70° C.) to wells and waiting 5 min before centrifugation into Microplates. DNA stocks were kept at −80° C. for long-term storage. The completed library contains genomic DNA isolated from 7,488 *actinomycete* strains.

Genetic Screen for pepM$^+$ Strains

The genomic DNA library was screened by PCR using four pairs of degenerate primers designed to amplify a 406-bp conserved fragment within bacterial pepM genes (forward: pepMF, CGCCGGCGTCTGCNTNGARGAYAA; reverse: pepMR, GCGCGCATCATGTGRTTNGCVYA; pepMX, GCGCGCATCATGTGGTTNGCCCADAT; pepMW, GCGCGCATCATGTGGTTNGCRTADAT; pepMZ, GCGCGCATCATGTTGTTNCCCCADAT). Promega Go Taq was used in 25 μL reactions containing 5 μM of each primer, 0.5 μL DMSO, and 0.5 μL template DNA. Thermocyclers were operated using the following program: 1) initial denaturation 3' at 98° C.; 2) 30" at 98° C.; 3) 30" at 58° C.; 4) 30" at 72° C.; 5) 3' at 72° C.; 6) hold at 12° C. Steps 2-4 were repeated for 35 cycles total. PCR amplification of the pepM fragment using the genomic DNA of *S. viridochromogenes* DSM 40736 (PTT producer), *S. luridus* NRRL 15101, and *S. rubellomurinus* ATCC 31215 was routinely performed to verify the integrity of reaction master mixes. PCR products were separated by electrophoresis through 1% agarose gels with the reaction products from positive controls flanking the edge of each side. The presence of a ~400 bp band, matching the size of the positive control reactions products indicated a positive result.

Genome Sequencing and Assembly

*Micromonospora* sp. SF-2312, *Saccharothrix* ST-888, *S. lavendulae* Fujisawa 8006, *S. rubellomurinus* subsp. *indigoferus* ATCC 31304, *S. rubellomurinus* ATCC 31215, and all initial PCR-positive strains from the NRRL collection were revived from freezer stocks on 172 agar plates and re-grown in 5-mL cultures as described above. Genomic DNA was isolated using the UltraClean-HTP Microbial DNA kit (MoBio, Carlsbad, Calif.) as described above except mycelia aggregates were first homogenized in microfuge tubes using sterile pestles. Paired-end, multiplexed sequencing libraries were constructed using Nextera DNA Sample Preparation Kits (Illumina, San Diego, Calif.) according to manufacturer directions. Samples were sequenced in multiple batches at either the University of Wisconsin Biotechnology Center (Illumina Genome Analyzer IIX) or the University of Illinois at Urbana-Champaign Roy Carver Biotechnology Center (Illumina Hi-Seq 2000, or MiSeq platforms). Sequencing reads produced from the GAIIX or the Hi-Seq with version 2 chemistry were assembled as previously described (Reference 33). ORF prediction for these genomes was performed with Prodigal version 2.50 (Reference 34). The genomes sequenced using the Illumina Hi-Seq with version 3 chemistry were assembled using IDBA UD version 1.0.9 (Reference 35) and ORF prediction was performed using Prodigal version 2.60. All sequenced strains originating from this study are listed herein. DNA sequences of all sequenced genomes have been deposited in GenBank under BioProject PRJNA238534, and are incorporated by reference herein in their entirety.

Phylogenetic Analysis

Assembled genomes were queried by BLAST to retrieve pepM sequences. Homologs from characterized phosphonate pathways were used to seed queries (*S. luridus* ACZ13456, *S. viridochromogenes* AAU00071, *S. fradiae* ACG70831, *S. rubellomurinus* ABB90393). The presence of the EDKxxxxxNS motif, the defining characteristic of bonafide pepMs from other members of the isocitrate lyase superfamily (Reference 36), was manually verified for all sequences. Alignments were performed using ClustalW in the MEGA software package (Reference 37). Approximated maximum-likelihood trees were constructed using FastTree 2 with gamma 20 correction (Reference 38) and displayed using FigTree. The sequence of 2-methylisocitrate lyase from *E. coli* K12 substrain MG1655 (NP_414865) was used as the outgroup.

Analysis of Phosphonate Gene-Clusters

Gene cluster family analysis was performed for phosphonate natural product biosynthetic gene clusters as in Doroghazi et al (Reference 30). Gene clusters were compared based on pepM amino acid identity, whole gene cluster alignments performed with PROmer (Reference 39) and the homologous genes shared by each pair of gene clusters. All gene clusters were manually examined to verify their integrity and that groups were appropriately assigned.

Rarefaction Analysis

MOTHUR was used for rarefaction analysis and calculations of species richness (Chao 1, Jackknife, Ace) (Reference 40). NRRL WC-3930, NRRL WC-3929, NRRL WC-3927, NRRL WC-3424, NRRL WC-3878, NRRL WC-3925, NRRL WC-3874, NRRL WC-3909, NRRL WC-3702, NRRL WC-3877, NRRL WC-3875, NRRL WC-3873, NRRL WC-3879, NRRL WC-3876, NRRL WC-3898, NRRL WC-3882, NRRL WC-3880, and NRRL WC-3900 are all mutants raised from of a parent strain *S. rimosus* subsp. *rimosus*, so accordingly, these pepM sequences were removed from analyses.

Extrapolation of Phosphonate Natural Product Discovery

The program estimateS was used for extrapolation of clustered amino acid and gene cluster family data (Reference 41). Amino acid similarity groups are calculated with MOTHUR (Reference 40) using a distance of 0.2 (80% similarity). Extrapolation was performed to a total of 1500 strains with 150 sampling points. For this analysis, each strain is considered a sampling location and each amino acid similarity group or gene cluster family is considered a species observation.

NMR and Mass Spectrometry

All NMR spectra were recorded at 25° C. on an Agilent DD2 600 MHz spectrometer (600 MHz for $^1$H, 150 MHz for $^{13}$C and 243 MHz for $^{31}$P) equipped with an OneNMR probe (Agilent). Proton and carbon chemical shifts are reported in δ values relative to an external standard of 0.1% tetramethylsilane in $D_2O$. Phosphorus shifts are reported in δ values relative to an external standard of 85% phosphoric acid. $^1$H-$^{31}$P gHMBC (gradient Heteronuclear Multiple-Bond Correlation) spectra were collected after optimization of long-range proton-phosphorus coupling at 18 Hz. An acquisition time of 1 s was used to obtain better spectral resolution. A total of 200 complex data points was collected in the F1 dimension. The spectrum was processed with a 90 degree shifted sine-bell square window function in MestReNova 7 software.

Mass spectrometry (except FTMS) was performed at the University of Illinois Mass Spectrometry Center. EI mass spectra were recorded on a 70-VSE spectrometer. ESI mass spectra were obtained on a Quattro spectrometer. LC-FTMS analysis of the samples was performed on a custom-made 11T LTQ-FT Ultra (ThermoFisher Scientific) equipped with a 1200 HPLC (Agilent) using a 2.1×150 mm Zic-pHILIC column (SeQuant). The samples were diluted 10-fold in 10 mM $NH_4HCO_3$ (pH=9.2) containing 90% acetonitrile. The injection volume was 20 μL. A gradient elution profile was used starting with 100% solvent B (10 mM $NH_4HCO_3$ containing 90% acetonitrile) for 2 min followed by a linear gradient to 50% solvent A (10 mM $NH_4HCO_3$ in water) over 13 min and then a return to initial conditions over 5 min and re-equilibration for 15 min before injection of the next sample. For high-resolution MS analyses, data were acquired in the FT cell at a nominal resolution of 50,000 and were summed over 1 min. Collisionally-induced dissociation (CID) spectra were acquired in the ion trap at 35% normalized collision energy and 30 ms activation time.

Initial Production Screen for Phosphonate Compounds

All pepM$^+$ *actinomycetes* from the USDA strain collection were cultivated in 20×150 mm test tubes containing 5 mL of ATCC172 on an angled roller drum (75 rpm) at 30° C. for five days. Cultures were then inoculated (200 μL) onto three ISP4 plates each. After 10 days of growth at 30° C., agar plates were frozen overnight at −20° C., thawed to room temperature, and compressed to harvest 40 mL of liquid from each strain. Phosphate mono- and di-esters were hydrolyzed by adding 50 U of calf intestinal alkaline phosphatase (New England Biolabs) and 2 mg of phosphodiesterase I (*Crotalus atrox;* Sigma-Aldrich) to extracts and incubating at 37° C. for two hours before freezing and lyophilization. Dried material was re-dissolved in 1 mL of $D_2O$ and stored at −20° C. until analysis. Phosphonates were detected from samples by resonances with chemical shifts of 8 ppm or greater in $^{31}$P NMR spectra (recorded for 800 scans).

Bioassays

Positive samples from the above $^{31}$P NMR screening were treated using iron-chelated Hypercel IMAC resin (Pall Corporation) as previously described to enrich for PnPs (Reference 14). Eluents were pH neutralized with acetic acid, lyophilized several times to remove residual volatile ammonium salts, and finally re-dissolved in 100 μL sterile Nanopure water. *E. coli* strain WM6242, that has the phosphonate uptake transporter genes (phnCDE) under the regulatory control of a $P_{tac}$ promoter, was seeded from exponentially growing cultures (25 μL, $OD_{600}$=0.4-0.5) into 5-mL M9-glucose soft agar and overlaid upon M9-glucose plates with and without 1 mM IPTG. 20 μL of samples were spotted onto 6 mm paper disks and placed onto the bioassay plates. After 18 hours incubation at 37° C., plates were inspected for zones of inhibition.

Antibiotic activity for purified PnPs was examined by growth inhibition in liquid cultures. *Salmonella typhimurium* LT2, *Escherichia coli* WM6242 (±1 mM IPTG), and *Pseudomonas aeruginosa* K were grown in M9-glucose. *Bacillus subtilis* subsp. *spizizenii* ATCC 6633, *Staphylococcus aureus* ATCC 25923, and *Mycobacterium smegmatis* NRRL B-14616 (37° C.) were cultivated in R2A. 96-Well plates containing 150 μL of media was inoculated with 1.5 uL of the appropriate cultures ($OD_{600}$=0.4-0.5). Kanamycin, aminomethylphosphonate, 1-hydroxy-2-aminoethylphosphonate, (R)-2,3-dihydroxypropylphosphonate, argolaphos A, and argolaphos B were added to a final concentration of 100 ug ml$^{-1}$. After growth for 16 hours (24 for *M. smegmatis*) in a shaking incubator (200 rpm), cell densities recorded on a Tecan microplate reader.

Antibiotic activity of argolaphos A and aminomethylphosphonate was also compared using disk-diffusion assays as described above, with the following modifications. 40 nmoles of each compound were dissolved in 20 μL of sterile water, spotted onto 6 mm paper disks, and placed onto plates seeded with WM6242. After 12 hours incubation at 37° C., plates were inspected for zones of inhibition.

Analysis of Phosphonate Metabolites from Cultures

Phosphonates were enriched from concentrated ISP4 supernatants of fosfomycin, plumbemycin, cyanohydromethylphosphonate, phosphonocystoximate, phosphonothrixin, fosfazinomycin, and dehydrophos strains using iron-chelated Hypercel IMAC resin (Pall Corporation) as previously described (Reference 14). Samples were then analyzed for phosphonate metabolites by LC-FTMS. A mass range of m/z 75-2000 was covered with a scan time of 1 s, and data were collected in the negative ion mode.

General Scale-Up Procedures for Phosphonate Production

Strains were inoculated in test tubes containing 5 mL of ATCC 172 on a roller drum (75 rpm) for five days before seeding (2 mL) into 500-mL Fernbach flasks containing 100 mL of the same medium. These were grown for five days on a platform shaker (200 rpm) and used to inoculate production media. Agar plates were inoculated with 200 μL of seed cultures with sterilized glass beads. 2 L and 4L Fernbach flasks containing 500 mL or 1 L of media, were inoculated with 10 or 20 mL of seed cultures, respectively, and grown on a platform shaker (200 rpm). All cultures were grown at 30° C.

Compounds of the Present Invention

The following compounds 1-11 of the present invention were isolated, purified, and identified. The compounds of the present invention can be prepared using known chemical transformations adapted to the particular situation at hand. Compounds 1-11 and additional Compounds 12-14 are shown herein. Also contemplated herein are pharmaceutically acceptable salts, esters, and prodrugs of Compounds 1-14, as well as mixtures thereof,

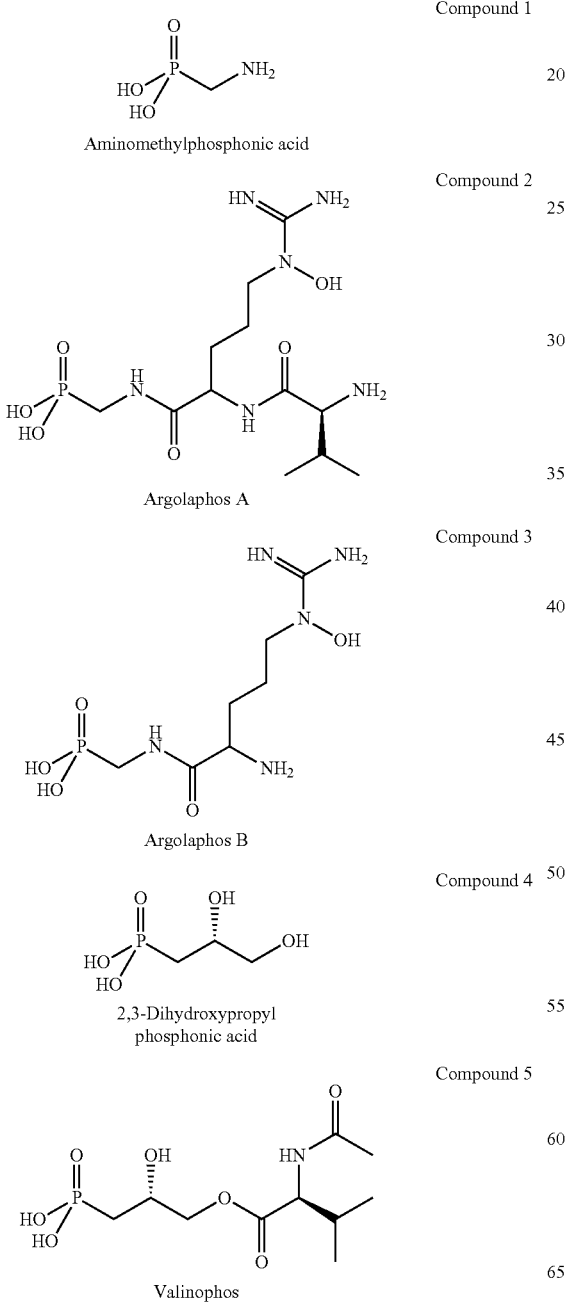

Compound 1 — Aminomethylphosphonic acid
Compound 2 — Argolaphos A
Compound 3 — Argolaphos B
Compound 4 — 2,3-Dihydroxypropyl phosphonic acid
Compound 5 — Valinophos

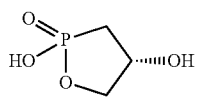

Compound 6 — 2,4-Dihydroxy-1,2-oxaphospholane 2-oxide

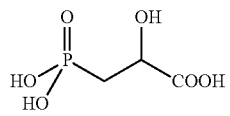

Compound 7 — 2-Hydroxy-3-phosphono propanoic acid

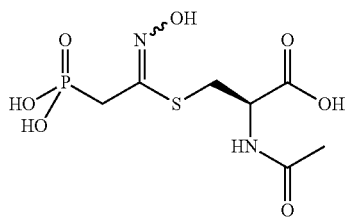

Compound 8 — Phosphonocystoximic acid

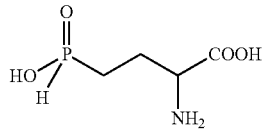

Compound 9 — Desmethylphosphinothricin

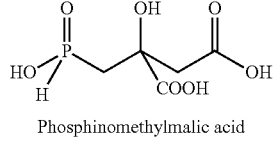

Compound 10 — Phosphinomethylmalic acid

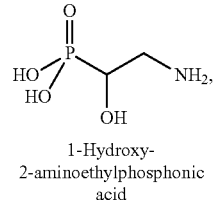

Compound 11 — 1-Hydroxy-2-aminoethylphosphonic acid

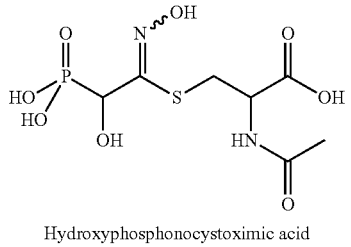

Compound 12 — Hydroxyphosphonocystoximic acid

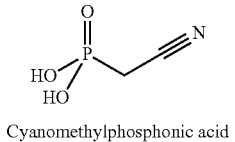

Compound 13 — Cyanomethylphosphonic acid

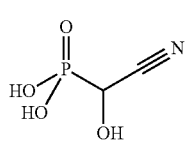

Compound 14

Hydroxycyanomethylphosphonic acid

Isolation and Purification of Compounds 1-3 from *S. monomycini* NRRL B-24309

NRRL B-24309 was grown in 16 L of liquid ISP4 and 20 L of ISP4 plates for 10 days. Agar plates were frozen overnight at −20° C., thawed to room temperature, and compressed using cheesecloth to recover 15 L of liquid extract. Additional metabolites were extracted from the residual agar by soaking with 5 L of methanol for 30 minutes. Liquid cultures were harvested by centrifugation and methanolic extracts of cell pellets combined with the clarified supernatant.

All liquid fractions were combined and concentrated 30-fold by rotary evaporation. A total of 3.6 liters of methanol was added to produce a final concentration of 75% methanol and then incubated overnight at −20° C. to facilitate precipitation. Insoluble material was removed by centrifugation and the supernatant concentrated by rotary evaporation to 500 mL. The material was then diluted 1:1 with deionized (dI) water and divided into four centrifuge bottles each containing 25 g of wetted charcoal powder. Samples were agitated for 10 minutes and then centrifuged. Supernatants were collected and set aside. The residual charcoal was then sequential washed with 400 mL of dI water (three times), 400 mL of 50% aqueous methanol, and finally 400 mL 75% aqueous methanol (three times). Each time, samples were agitated after the addition of solvent and then centrifuging to re-sediment charcoal powder. Unbound material was combined with supernatants from the first water, 50%, and 75% methanol washes, filtered to removal residual charcoal powder, and concentrated to 400 mL by rotary evaporation.

A total volume of 3.6 liters of methanol was added to produce a final concentration of 90% methanol. Insoluble material was removed by centrifugation, and the supernatant was concentrated to dryness and the residue dissolved in 100 mL of 0.1% aqueous acetic acid, which was applied to a 50 mL Fe(III) IMAC gravity column. Before sample loading the column was equilibrated with 0.1% aqueous acetic acid. After sample loading, the column was washed successively with 5 volumes of 0.1% aqueous acetic acid and 0.1% aqueous acetic acid in 20% acetonitrile/80% water. The materials were eluted from the column with 100 mM aqueous $NH_4HCO_3$. The eluate (200 mL) from the iron IMAC column was dried with a rotary evaporator.

The materials were dissolved in 20 mL of distilled $H_2O$ and then chromatographed over a glass Sephadex LH-20 column (42×1400 mm gel bed) eluted with distilled $H_2O$ (flow: 200 mL/h; fractions: 10 mL) to yield 175 fractions. Based on $^{31}P$ NMR analysis of each fraction, fractions 1 to 55 were combined as fraction A, fractions 55 to 66 were combined as fraction B, fractions 67 to 84 were combined as fraction C, fractions 85 to 129 were combined as fraction D, and fractions 130 to 175 were combined as fraction E. All fractions were dried with a rotary evaporator. Fraction C was dissolved in 1 mL of distilled $H_2O$ and then chromatographed over a glass Sephadex LH-20 column (25×1200 mm gel bed) eluted with distilled $H_2O$ (flow: 30 mL/h; fractions: 10 mL) to yield 40 fractions. Based on $^{31}P$ NMR analysis of each fraction, fractions 25 to 30 were combined and dried with a rotary evaporator to give about 1.5 mg of compound 1 (for the structures of all numbered compounds.

Fraction B (30 mg) was dissolved in 1 mL of distilled $H_2O$ and further purified using a 10×250 mm HILIC column (Atlantis® HILIC Silica, 5 μm) and a gradient elution, yielding compounds 2 (20 mg) and 3 (1 mg). The gradient used was: 20 min at 100% solvent B (0.1% TFA in acetonitrile) then a linear gradient to 60% solvent A (0.1% TFA in distilled $H_2O$) over 40 min. The flow rate was 3 mL/min. The retention time for compounds 2 and 3 was 35 and 37 min.

Structure Elucidation of Compounds 1-3

Compound 1 was identical to aminomethylphosphonic acid, as shown by its NMR and MS data, which matched those of an authentic standard. Compound 2 was obtained as a white, amorphous solid, and the molecular formula was confirmed by negative mode high-resolution ESIMS (observed m/z 381.1662; calcd for $C_{12}H_{26}O_6N_6P$, 381.1657, which is consistent with four degrees of unsaturation. Compound 2 was dissolved in DMSO-$d_6$ with one equivalent of TFA. The $^1H$ NMR spectrum showed 24 resonances due to the presence of six methyl protons ($\delta_H$ 0.92), eight methylene protons ($\delta_H$ 1.54-3.64), three methine protons ($\delta_H$ 2.04, 3.67 and 4.45) and seven amino or amide protons ($\delta_H$ 7.6-8.5). The signals were confirmed by $^1H$-$^{15}N$ HSQC correlation. The seven amine or amide protons disappeared when compound 2 was dissolved in $D_2O$ (FIG. S18) because of exchange of those protons with deuterium (Table S3). A $^1H$-$^1H$ TOCSY spectrum showed that compound 2 is made up of two amino acids including valine ($\delta_H$ 3.67, 2.04 and 0.92) and $N^5$-hydroxyl arginine ($\delta_H$ 4.45, 1.67, 1.54, 1.72, 1.56, 3.46). The hydroxyl position in arginine was determined by $^1H$-$^{15}N$ HSQC correlation because no proton was observed on $N^5$ of arginine. $^1H$-$^{31}P$ HMBC spectra indicated that compound 2 contained aminomethylphosphonic acid because the phosphorus was correlated to two methylene protons ($\delta_H$ 3.28, 3.46) and one amide proton ($\delta_H$ 8.21). In the $^1H$-$^{13}C$ HMBC spectrum, this amide proton ($\delta_H$ 8.21) correlated with one carbonyl carbon ($\delta c$ 170.5), which belonged to $N^5$-hydroxyl arginine. Therefore, compound 2 was composed of aminomethylphosphonic acid, $N^5$-hydroxyl arginine and valine, which were connected by two amide bonds. All NMR data including $^1H$, $^{13}C$, $^{31}P$, DEPT 135°, $^1H$-$^{13}C$ HSQC, $^1H$-$^{31}P$ HMBC, $^1H$-$^{13}C$ HMBC, $^1H$-$^1H$ COSY, $^1H$-$^1H$ TOCSY and $^1H$-$^{15}N$ HSQC spectrum were consistent with the structure. The structure of compound 2 was also confirmed by tandem MS data.

Compound 3 was obtained as a white, amorphous solid, and the molecular formula was confirmed by analysis of the negative mode high-resolution ESIMS (observed m/z 282.0971; calcd for $C_7H_{17}O_5N_5P$, 282.0973; FIG. S36). The $^1H$ and $^{13}C$ spectra of compound 3 were similar to those of compound 2. The mass difference of 99 Da suggested that the only difference between compounds 2 and 3 is one valine group, which was confirmed by a $^1H$-$^1H$ TOCSY spectrum showing the absence of the spin system of the valine moiety. Therefore, compound 3 was composed of aminomethylphosphonic acid and $N_5$-hydroxyl arginine, which were connected by one amide bond. All NMR data were consistent with structure 3.

Isolation and Purification of Compounds 4-7 from *S. durhamensis* NRRL B-3309

NRRL B-3309 was grown in 10 L of liquid GUBC and 40 L of GUBC plates for 12 days. Agar plates were frozen overnight at −20° C., thawed to room temperature, and compressed using cheesecloth to recover 30 L of liquid extract. Additional metabolites were extracted from the residual agar by soaking with 10 L of methanol for 30 minutes. Liquid cultures were harvested by centrifugation and methanolic extracts of cell pellets combined with the clarified supernatants. This was concentrated by rotary evaporation to about 2 L, to which 8 L of methanol was added to produce a final concentration of 80% methanol. After the precipitate was removed by centrifugation, the supernatant was concentrated to about 1 L. A total volume of 4 L of methanol was added to repeat the step above.

The liquid was concentrated to dryness and dissolved in 200 mL of 0.1% aqueous acetic acid, which was then applied to a 100 mL Fe(III) IMAC gravity column. Before sample loading the column was equilibrated with 0.1% acetic acid. After sample loading, the column was washed successively with 5 volumes of 0.1% acetic acid and 0.1% acetic acid in 20% acetonitrile (ACN). The materials were eluted from the column with 100 mM aqueous $NH_4HCO_3$. The eluate (200 mL) from the iron IMAC column was dried with a rotary evaporator as fraction 1. The unabsorbed sample was also dried as fraction 2. Fraction 2 contained compound 6, however, no methods were found to be effective for purification of compound 6 because it was unstable and easily decomposed in the course of purification.

Fraction 1 was dissolved in 50 mL of distilled $H_2O$ and then chromatographed over a glass Sephadex G-25 column (65×1800 mm gel bed) eluted with distilled $H_2O$ (flow: 200 mL/h; fractions: 10 mL) to yield 150 fractions. Based on $^{31}P$ NMR analysis of each fraction, fractions 1 to 60 were combined as fraction A-1, fractions 61 to 68 were combined as fraction A-2, fractions 69 to 98 were combined as fraction A-3, fractions 99 to 126 were combined as fraction A-4, and fractions 127 to 150 were combined as fraction A-5. All fractions were dried with a rotary evaporator. Fraction A-3 was dissolved in 1 mL of distilled $H_2O$ and then chromatographed over a glass Sephadex G-25 column (25×1800 mm gel bed) eluted with distilled $H_2O$ (flow: 30 mL/h; fractions: 10 mL) to yield 35 fractions. Based on $^{31}P$ NMR analysis for each fraction, fractions from 22 to 24 were combined and dried with a rotary evaporator to give about 1 mg of a mixture of compounds 4 and 5. Fractions 26 contained compound 7 (100 μg). Fractions 28 to 30 were combined, dried and dissolved in 0.5 mL of $H_2O$. Then the sample was directly subjected to semipreparative fractionation by HILIC HPLC on an Atlantis® HILIC Silica column (250×10 mm, 5 μm) using a program of MeCN—$H_2O$ 0-10 min (95:5), followed by a linear gradient to 100% $H_2O$ over 60 min at a flow rate of 4 mL/min and a temperature of 23° C., to yield compound 4 (1 mg) with a retention time of 26 min.

Structure Elucidation of Compounds 4-7

The molecular formula $C_3H_9O_5P$ of compound 4 was confirmed by analysis of the positive mode high-resolution ESIMS (observed m/z 155.0115; calcd for $C_3H_8O_5P$, 155.0115; FIG. S46). Compound 4 was identical to 2,3-dihydroxypropanoic acid, as shown by its NMR and MS data, which matched those of a synthetic standard. The molecular formula $C_{10}H_{20}O_7NP$ of compound 5 was confirmed by analysis of the positive mode high-resolution ESIMS (observed m/z 298.1051; calcd for $C_{10}H_{21}O_7NP$, 298.1050; FIG. S50). A $^1H$-$^{31}P$ HMBC spectrum of the mixture of compounds 4 and 5 indicated that both compounds shared similar structural features. A $^1H$-$^1H$ TOCSY spectrum showed that compound 5 contained one valine group ($\delta_H$ 4.20, 2.10 and 0.83). Therefore, the mass difference of 141 Da between compounds 4 and 5 resulted from an additional N-acetyl valine in compound 5, which was confirmed by the correlation of H-1' ($\delta_H$ 4.21) with C-1" ($\delta_C$ 180.0) and H-2" ($\delta_H$ 1.93) with C-1" in a $^1H$-$^{13}C$ HMBC spectrum. N-Acetyl valine was linked with compound 4 by an ester bond formed between the carboxylic acid of N-acetyl valine and the 3-hydroxyl group of compound 4, which was confirmed by the correlation of H-3 ($\delta_H$ 4.04 and 4.19) with C-1' ($\delta_C$ 175.9) in the $^1H$-$^{13}C$ HMBC spectrum. Therefore, compound 5 was made up of 2,3-hydroxypropanoic acid and N-acetyl valine, which was connected by one ester bond. All NMR data including $^1H$, $^{13}C$, 31P, DEPT 135°, $^1H$–$^{13}C$ HSQC, $^1H$–$^{31}P$ HMBC, $^1H$-$^{13}C$ HMBC, $^1H$-$^1H$ COSY and $^1H$-$^1H$ TOCSY are consistent with this structure.

Compound 6 was cyclic 2,3-dihydroxypropanoic acid, as shown by its NMR data, which matched those reported in the literature (Reference 42).

Compound 7 was 2-hydroxy-3-phosphonopropionate, as shown by its NMR data.

Isolation and Purification of Compound 8 from *Streptomyces* sp. NRRL S-481

NRRL S-481 was grown in 50 L of liquid ISP4 for 10 days. Cultures were centrifuged, the clarified supernatant frozen and then lyophilized. A total volume of 5 L of 90% aqueous methanol was added to the dried material. After the precipitate was removed by centrifugation, the supernatant was concentrated to dryness with a rotary evaporator and 1 L of 90% methanol was added. After the precipitate formed was removed, the supernatant was concentrated to dryness with a rotary evaporator.

The residue was dissolved in 50 mL of distilled $H_2O$ and then chromatographed over a glass Sephadex G-25 column (65×1800 mm gel bed) eluted with distilled $H_2O$ (flow: 200 mL/h; 10 mL/vial) to yield 150 vials. Based on $^{31}P$ NMR analysis of each vial, vials 1 to 54 were combined as fraction 1, vials 55 to 65 were combined as fraction 2, vials from 66 to 95 were combined as fraction 3, vials 96 to 125 were combined as fraction 4, and vials 126 to 150 were combined as fraction 5. All fractions were dried with a rotary evaporator. Fraction 2 was dissolved in 3 mL of distilled $H_2O$ and then chromatographed over a glass Sephadex LH-20 column (25×1800 mm gel bed) eluted with distilled $H_2O$ (flow: 30 mL/h; 10 mL/vial) to yield 40 vials. Based on $^{31}P$ NMR analysis for each vial, the contents of vials 10 to 20 were combined and dried with a rotary evaporator. The residue was dissolved in 2 mL of distilled $H_2O$ and then chromatographed over a glass Sephadex G-25 column (25×1800 mm gel bed) eluted with distilled $H_2O$ (flow: 30 mL/h; 10 mL/vial) to yield 30 vials. Based on $^{31}P$ NMR analysis of each vial, the contents of vials 9 to 13 were combined and dried with a rotary evaporator. The residue was dissolved in 1 mL of distilled $H_2O$ and then chromatographed over a glass Sephadex LH-20 column (25×1200 mm gel bed) eluted with distilled $H_2O$ (flow: 30 mL/h; 10 mL/vial) to yield 30 vials. Based on $^{31}P$ NMR analysis of each vial, vial 7 contained compound 8.

Structure Elucidation of Compound 8

The molecular formula $C_7H_{13}O_7N_2P$ of compound 8 was confirmed by analysis of the negative high-resolution ESIMS (observed m/z 299.0108; calcd for $C_7H_{13}O_7N_2PS$, 299.0108), which is consistent with four degrees of unsaturation. The $^1H$ NMR spectrum (Table 5) showed eight resonances due to the presence of three methyl protons ($\delta_H$ 1.91), four methylene protons ($\delta_H$ 2.66-3.48), and one methine proton ($\delta_H$ 4.25). Five protons of compound 8 exchanged with deuterium in $D_2O$ so that they were not available in the $^1H$ NMR spectrum. A $^1H$-$^1H$ TOCSY spectrum strongly suggested that compound 8 contained one cysteine group ($\delta_H$ 4.25, 3.28 and 3.48; FIG. S67). The presence of a thiohydroximate moiety in compound 8 was inferred from the presence of a characteristic $^{13}$C signal at 153.5 ppm. The presence of an acetyl moiety was confirmed by the correlation of H-2" ($\delta_H$ 1.91) with C-1" ($\delta$c 173.6) in the $^1$H-$^{13}$C HMBC spectrum (FIG. S68). Therefore, compound 8 was assigned as a thiohydroximate-containing compound. All NMR data including $^1$H, $^{31}$P, $^1$H$^{13}$C HSQC, $^1$H-$^{31}$P HMBC, $^1$H-$^{13}$C HMBC, $^1$H-$^1$H COSY and $^1$H-$^1$H TOCSY are consistent with the structure.

Isolation and Purification of Compounds 9 and 10 from *Nonomurea candida* NRRL B-24552

NRRL B-24552 was grown on 50 L of GUBC plates for 10 days. Agar plates were frozen overnight at −20° C., thawed to room temperature, and compressed using cheesecloth to recover 35 L of liquid extract. Additional metabolites were extracted from the residual agar by soaking with 10 L of methanol for 30 minutes. All liquids were combined and concentrated by rotary evaporation to about 2 L. A total volume of 6 L of methanol was added to produce a final concentration of 75% aqueous methanol. After the precipitate was removed by centrifugation, the supernatant was concentrated to about 500 mL and stored at −20° C. until further processing.

The material was concentrated by rotary evaporation and dried material dissolved in 50 mL of distilled H$_2$O and then chromatographed over a glass Sephadex LH-20 column (25×1800 mm gel bed) eluted with distilled H$_2$O (flow: 30 mL/h; 10 mL/vial) to yield 40 vials. Based on $^{31}$P NMR analysis for each vial, the contents of vials 25 to 32 were combined and dried with a rotary evaporator. The residue was dissolved in 2 mL of distilled H$_2$O and then chromatographed over a glass Sephadex LH-20 column (25×1200 mm gel bed) eluted with distilled H$_2$O (flow: 200 mL/h; fractions: 10 mL) to yield 40 fractions. Based on $^{31}$P NMR analysis of each vial, the contents of vials 16 to 21 were combined and the sample was compound 10 (0.1 mg). Vials 25 to 32 were combined and the sample was compound 9 (0.2 mg).

Structure Elucidation of Compound 9 and 10

Compound 9 was determined to be desmethylphosphinothricin as shown by its NMR data which matched those reported in the literature (Reference 28).

Compound 10 was 2-phosphinomethylmalic acid as shown by its NMR data which matched those reported in the literature (Reference 43).

Isolation and Purification of Compound 11 from *S. californicus* NRRL B-1221 NRRL B-1221 was grown in 30 L of liquid R2AS supplemented with 5 mM N-acetylglucosamine for 10 days. Cultures were harvested by centrifugation, clarified supernatants frozen and then lyophilized. Dried material was re-dissolved in 1 L of dI water and a total volume of 3 L of methanol was added to a final concentration of 75% methanol. The sample was incubated at −20° C. overnight to promote the formation of precipitates, which were removed by centrifugation. The supernatant was concentrated to about 500 mL and a total volume of 1.5 L of methanol added to repeat the step above. The sample was concentrated to a volume of 400 mL and stored at −20° C. until further processing.

The material was concentrated to dryness and the residue dissolved in 200 mL of 0.1% aqueous acetic acid, which was applied to a 50 mL Fe(III) IMAC gravity column. Before sample loading the column was equilibrated with 0.1% aqueous acetic acid. After sample loading, the column was washed successively with 5 volumes of 0.1% aqueous acetic acid and 0.1% aqueous acetic acid in 20% acetonitrile/80% water. The materials were eluted from the column with 100 mM aqueous NH$_4$HCO$_3$. The eluate (500 mL) from the iron IMAC column was dried with a rotary evaporator.

The materials were dissolved in 20 mL of distilled H$_2$O and then chromatographed over a glass Sephadex G-25 column (25×1200 mm gel bed) eluted with distilled H$_2$O (flow: 200 mL/h; fractions: 10 mL) to yield 30 fractions. Based on $^{31}$P NMR analysis of each fraction, fractions 15 to 27 were combined and dried with a rotary evaporator. The sample was dissolved in 1 mL of distilled H$_2$O and then chromatographed over a glass Sephadex LH-20 column (25×1200 mm gel bed) eluted with distilled H$_2$O (flow: 30 mL/h; fractions: 10 mL) to yield 40 fractions. Based on $^{31}$P NMR analysis of each fraction, fraction 11 was dried with a rotary evaporator to give about 0.1 mg of compound 11.

Structure Elucidation of Compound 11

Compound 11 was 1-hydroxy-2-aminoethylphosphoric acid, as shown by its NMR data which matched those reported in the literature (Reference 44).

Marfey's Reagent for Analysis of Compounds 2, 3, 5 and 8

Marfey's reagent is generally used for the chiral analysis of amino acids and peptides. A sample of about 0.2 mg of peptide was hydrolyzed by treatment with 2 mL of 6 N HCl and heating to 120° C. for 24 h in a sealed ampule (Reference 45). The hydrolysate was dried under N$_2$. In an Eppendorf tube, 3.6 µmol of a 1% acetone solution of FDAA (N-(5-fluoro-2,4-dinitrophenyl)-D-alaninamide) and 20 µmol of a 1 M solution of NaHCO$_3$ were added to 2.5 µmol of amino acid. The reaction mixture was heated with frequent shaking over a hot plate at 40° C. for 1 h and then cooled to RT. Then, 20 µmol of 2 M HCl and 1 mL of MeOH were added to the reaction mixture. The samples were analyzed by LC-MS, and molecular weights and retention times were compared with those of standard amino acids. Acetonitrile/water containing 0.05% HCOOH was used as the mobile phase with a linear gradient elution mode (MeCN, 10-60%, 60 min) at a flow rate of 0.6 mL/min. A mass range of m/z 100-3000 was covered with a scan time of 1 s, and data were collected in the positive ion mode.

Hydrolysis and Marfey's analysis of compounds 5 and 8 were carried out as described above. The absolute configuration of valine in compound 5 and cysteine in compound 8 was determined to be L.

Absolute Configuration of Compound 4

The specific rotation of compound 4 was observed as $[\alpha]_D$+4.5 (c 1.0, H$_2$O). Therefore the absolute configuration of compound 4 is R by comparison with specific rotation of synthetic (R) and (S)-2,3-dihydroxypropanoic acid in the literature (Reference 46).

REFERENCES AND NOTES

1. G. M. Cragg, D. J. Newman, Natural products: a continuing source of novel drug leads. *Biochim. Biophys. Acta* 1830, 3670-3695 (2013).
2. B. O. Bachmann, S. G. Van Lanen, R. H. Baltz, Microbial genome mining for accelerated natural products discovery: is a renaissance in the making? *J. Ind. Microbiol. Biotechnol.* 41, 175-184 (2014).
3. G. L. Challis, Genome mining for novel natural product discovery. *J. Med. Chem.* 51, 2618-2628 (2008).
4. H. B. Bode, R. Muller, The impact of bacterial genomics on natural product research. *Angew. Chem. Int. Ed.* 44, 6828-6846 (2005).

5. W. W. Metcalf, W. A. van der Donk, Biosynthesis of phosphonic and phosphinic acid natural products. *Annu. Rev. Biochem.* 78, 65-94 (2009).
6. J. Berdy, Thoughts and facts about antibiotics: where we are now and where we are heading. *J. Antibiot.* 65, 385-395 (2012).
7. K. S. Ju, J. R. Doroghazi, W. W. Metcalf, Genomics-enabled discovery of phosphonate natural products and their biosynthetic pathways. *J. Ind. Microbiol. Biotechnol.* 41, 345-356 (2013).
8. A. C. Eliot, B. M. Griffin, P. M. Thomas, T. W. Johannes, N. L. Kelleher, H. Zhao, W. W. Metcalf, Cloning, expression, and biochemical characterization of *Streptomyces rubellomurinus* genes required for biosynthesis of antimalarial compound FR900098. *Chem. Biol.* 15, 765-770 (2008).
9. J. A. Blodgett, J. K. Zhang, W. W. Metcalf, Molecular cloning, sequence analysis, and heterologous expression of the phosphinothricin tripeptide biosynthetic gene cluster from *Streptomyces viridochromogenes* DSM 40736. *Antimicrob. Agents Chemother.* 49, 230-240 (2005).
10. R. D. Woodyer, Z. Shao, P. M. Thomas, N. L. Kelleher, J. A. Blodgett, W. W. Metcalf, W. A. van der Donk, H. Zhao, Heterologous production of fosfomycin and identification of the minimal biosynthetic gene cluster. *Chem. Biol.* 13, 1171-1182 (2006).
11. S. A. Borisova, B. T. Circello, J. K. Zhang, W. A. van der Donk, W. W. Metcalf, Biosynthesis of rhizocticins, antifungal phosphonate oligopeptides produced by *Bacillus subtilis* ATCC6633. *Chem. Biol.* 17, 28-37 (2010).
12. B. T. Circello, C. G. Miller, J. H. Lee, W. A. van der Donk, W. W. Metcalf, The antibiotic dehydrophos is converted to a toxic pyruvate analog by peptide bond cleavage in *Salmonella enterica*. *Antimicrob. Agents Chemother.* 55, 3357-3362 (2011).
13. X. Yu, J. R. Doroghazi, S. C. Janga, J. K. Zhang, B. Circello, B. M. Griffin, D. P. Labeda, W. W. Metcalf, Diversity and abundance of phosphonate biosynthetic genes in nature. *Proc. Natl. Acad. Sci. USA* 110, 20759-20764 (2013).
14. B. S. Evans, C. Zhao, J. Gao, C. M. Evans, K. S. Ju, J. R. Doroghazi, W. A. van der Donk, N. L. Kelleher, W. W. Metcalf, Discovery of the antibiotic phosacetamycin via a new mass spectrometry-based method for phosphonic acid detection. *ACS Chem. Biol.* 8, 908-913 (2013).
15. M. L. Nielsen, J. V. Pustinger, J. Strobel, Phosphorus-31 nuclear magnetic resonance chemical shifts of phosphorus compounds. *J. Chem. Eng. Data* 9, 167-170 (1964).
16. Materials and methods are available as supplementary materials on *Science* online.,
17. E. Takahashi, T. Kimura, K. Nakamura, M. Arahira, M. Lida, Phosphonothrixin, a novel herbicidal antibiotic produced by *Saccharothrix* sp. ST-888. I. Taxonomy, fermentation, isolation and biological properties. *J. Antibiot.* 48, 1124-1129 (1995).
18. H. Watanabe, J. Yoshida, E. Tanaka, M. Ito, S. Miyadoh, T. Shomura, Studies on a new phosphonic acid antibiotic, SF-2312. *Sci. Rep. Meiji Seika Kaisha* 25, 12-17 (1986).
19. M. Okuhara, Y. Kuroda, T. Goto, M. Okamoto, H. Terano, M. Kohsaka, H. Aoki, H. Imanaka, Studies on new phosphonic acid antibiotics. I. FR-900098, isolation and characterization. *J. Antibiot.* 33, 13-17 (1980).
20. M. Okuhara, Y. Kuroda, T. Goto, M. Okamoto, H. Terano, M. Kohsaka, H. Aoki, H. Imanaka, Studies on new phosphonic acid antibiotics. III. Isolation and characterization of FR-31564, FR-32863 and FR-33289. *J. Antibiot.* 33, 24-28 (1980).
21. J. A. Blodgett, P. M. Thomas, G. Li, J. E. Velasquez, W. A. van der Donk, N. L. Kelleher, W. W. Metcalf, Unusual transformations in the biosynthesis of the antibiotic phosphinothricin tripeptide. *Nat. Chem. Biol.* 3, 480-485 (2007).
22. H. Maehr, J. F. Blount, D. L. Pruess, L. Yarmchuk, M. Kellett, Antimetabolites produced by microorganisms. 8. N5-hydroxy-L-arginine, a new naturally occurring amino acid. *J. Antibiot.* 26, 284-288 (1973).
23. D. Perlman, A. J. Vlietinck, H. W. Matthews, F. F. Lo, Microbial production of vitamin B12 antimetabolites. I. N5-hydroxy-L-arginine from *Bacillus cereus* 439. *J. Antibiot.* 27, 826-832 (1974).
24. B. Fischer, W. Keller-Schierlein, H. Kneifel, W. A. Konig, W. Loeffler, A. Muller, R. Muntwyler, H. Zahner, [Metabolic products of microorganisms. 118. Delta-N-hydroxy-L-arginine, an amino acid antagonist from *Nannizzia gypsea*]. *Arch. Mikrobiol.* 91, 203-220 (1973).
25. F. R. Atherton, M. J. Hall, C. H. Hassall, R. W. Lambert, W. J. Lloyd, P. S. Ringrose, D. Westmacott, Antibacterial activity and mechanism of action of phosphonopeptides based on aminomethylphosphonic acid. *Antimicrob. Agents Chemother.* 22, 571-578 (1982).
26. J. P. Cioni, J. R. Doroghazi, K. S. Ju, X. Yu, B. S. Evans, J. Lee, W. W. Metcalf, Cyanohydrin Phosphonate Natural Product from *Streptomyces regensis*. *J. Nat. Prod.* 77, 243-249 (2014).
27. B. A. Halkier, J. Gershenzon, Biology and biochemistry of glucosinolates. *Annu. Ren. Plant Biol.* 57, 303-333 (2006).
28. H. Seto, T. Sasaki, S. Imai, T. Tsuruoka, H. Ogawa, A. Satoh, S. Inouye, T. Niida, N. Otake, Studies on the biosynthesis of bialaphos (SF-1293). 2. Isolation of the first natural products with a C—P—H bond and their involvement in the C—P—C bond formation. *J. Antibiot.* 36, 96-98 (1983).
29. X. Yu, N. P. Price, B. S. Evans, W. W. Metcalf, Purification and characterization of phosphonoglycans from *Glycomyces* sp. strain NRRL B-16210 and *Stackebrandtia nassauensis* NRRL B-16338. *J. Bacteriol.* 196, 1768-1779 (2014).
30. J. R. Doroghazi, J. C. Albright, A. W. Goering, K.-S. Ju, R. R. Haines, K. A. Tchulukov, D. P. Labeda, N. L. Kelleher, W. W. Metcalf, A roadmap for natural product discovery based on large-scale genomics and metabolomics. *Nat. Chem. Biol.*, Submitted (2014).
31. P. Gerhardt, R. G. E. Murray, W. A. Wood, N. R. Krieg, Eds., *Methods for general and molecular bacteriology*, (American Society for Microbiology, Washington, D.C., 1994), pp. 791.
32. R. Y. Stanier, N. J. Palleroni, M. Doudoroff, The aerobic pseudomonads: a taxonomic study. *J. Gen. Microbiol.* 43, 159-271 (1966).
33. J. R. Doroghazi, K. S. Ju, D. W. Brown, D. P. Labeda, Z. Deng, W. W. Metcalf, W. Chen, N. P. Price, Genome sequences of three tunicamycin-producing *streptomyces* strains, *S. chartreusis* NRRL 12338, *S. chartreusis* NRRL 3882, and *S. lysosuperificus* ATCC 31396. *J. Bacteriol.* 193, 7021-7022 (2011).

34. D. Hyatt, G. L. Chen, P. F. Locascio, M. L. Land, F. W. Larimer, L. J. Hauser, Prodigal: prokaryotic gene recognition and translation initiation site identification. *BMC Bioinformatics* 11, 119 (2010).

35. Y. Peng, H. C. Leung, S. M. Yiu, F. Y. Chin, IDBA-UD: a de novo assembler for single-cell and metagenomic sequencing data with highly uneven depth. *Bioinformatics* 28, 1420-1428 (2012).

36. C. C. Chen, Y. Han, W. Niu, A. N. Kulakova, A. Howard, J. P. Quinn, D. Dunaway-Mariano, O. Herzberg, Structure and kinetics of phosphonopyruvate hydrolase from *Variovorax* sp. Pa12: new insight into the divergence of catalysis within the PEP mutase/isocitrate lyase superfamily. *Biochemistry* 45, 11491-11504 (2006).

37. K. Tamura, G. Stecher, D. Peterson, A. Filipski, S. Kumar, MEGA6: Molecular Evolutionary Genetics Analysis version 6.0. *Mol. Biol. Evol.* 30, 2725-2729 (2013).

38. M. N. Price, P. S. Dehal, A. P. Arkin, FastTree 2-approximately maximum-likelihood trees for large alignments. *PLoS One* 5, e9490 (2010).

39. S. Kurtz, A. Phillippy, A. L. Delcher, M. Smoot, M. Shumway, C. Antonescu, S. L. Salzberg, Versatile and open software for comparing large genomes. *Genome Biol.* 5, R12 (2004).

40. P. D. Schloss, S. L. Westcott, T. Ryabin, J. R. Hall, M. Hartmann, E. B. Hollister, R. A. Lesniewski, B. B. Oakley, D. H. Parks, C. J. Robinson, J. W. Sahl, B. Stres, G. G. Thallinger, D. J. Van Horn, C. F. Weber, Introducing mothur: open-source, platform-independent, community-supported software for describing and comparing microbial communities. *Appl. Environ. Microbiol.* 75, 7537-7541 (2009).

41. R. K. Colwell, A. Chao, N. J. Gotelli, S.-Y. Lin, C. X. Mao, R. L. Chazdon, J. T. Longino, Models and estimators linking individual-based and sample-based rarefaction, extrapolation, and comparison of assemblages. *J. Plant Ecol.* 5, 3-21 (2012).

42. S. V. Serves, D. N. Sotiropoulos, P. V. Ioannou, Reaction of tris(trimethylsilyl) phosphite with epoxides and glycidol derivatives. *Phosphorus, Sulfur Silicon Relat. Elem.* 107, 27-31 (1995).

43. H. Seto, S. Imai, T. Sasaki, K. Shimotohno, T. Tsuruoka, H. Ogawa, A. Satoh, S. Inouye, T. Niida, N. Otake, Studies on the biosynthesis of bialaphos (SF-1293). 5. Production of 2-phosphinomethylmalic acid, an analogue of citric acid by *Streptomyces hygroscopicus* SF-1293 and its involvement in the biosynthesis of bialaphos. *J. Antibiot.* 37, 1509-1511 (1984).

44. T. Tone, Y. Okamoto, H. Sakurai, Preparation of 1-hydroxy-2-aminoethylphosphonic acid and its alkyl-substituted derivatives. *Chem. Lett.* 7, 1349-1350 (1978).

45. P. Marfey, Determination of D-amino acids. 2. Use of a bifunctional reagent, 1,5-difluoro-2,4-dinitrobenzene. *Carlsberg Res. Commun.* 49, 591-596 (1984).

46. E. Baer, H. Basu, Phosphonic acid analogues of carbohydrate metabolites. I. Synthesis of L-and D-dihydroxypropylphosphonic acid. *Can. J. Biochem.* 47, 955-960 (1969).

47. W. Liu, J. Ahlert, Q. Gao, E. Wendt-Pienkowski, B. Shen, J. S. Thorson, Rapid PCR amplification of minimal enediyne polyketide synthase cassettes leads to a predictive familial classification model. *Proc. Natl. Acad. Sci. USA* 100, 11959-11963 (2003).

48. Krug D & Müller R (2014) Secondary metabolomics: the impact of mass spectrometry-based approaches on the discovery and characterization of microbial natural products. *Nat Prod Rep* 31(6):768-783.

49. Forseth R R & Schroeder F C (2011) NMR-spectroscopic analysis of mixtures: from structure to function. *Curr Opin Chem Biol* 15(1):38-47.

50. Hove-Jensen B, Zechel D L, & Jochimsen B (2014) Utilization of glyphosate as phosphate source: biochemistry and genetics of bacterial carbon-phosphorus lyase. *Microbiol Mol Biol Rev* 78(1):176-197.

51. Hakala M T, Glaid A J, & Schwert G W (1956) Lactic dehydrogenase. II. Variation of kinetic and equilibrium constants with temperature. *J Biol Chem* 221(1):191-209.

52. Philmus B, Guerrette J P, & Hemscheidt T K (2009) Substrate specificity and scope of MvdD, a GRASP-like ligase from the microviridin biosynthetic gene cluster. *ACS Chem Biol* 4(6):429-434.

ADDITIONAL REFERENCES

Koehn F E & Carter G T (2005) The evolving role of natural products in drug discovery. *Nat Rev Drug Discov* 4(3):206-220.

Brotz-Oesterhelt H & Sass P (2010) Postgenomic strategies in antibacterial drug discovery. *Future Microbiol* 5(10):1553-1579.

Baltz R H (2006) Marcel Faber Roundtable: is our antibiotic pipeline unproductive because of starvation, constipation or lack of inspiration? *J Ind Microbiol Biotechnol* 33(7):507-513.

Abdelmohsen U R, et al. (2015) Elicitation of secondary metabolism in *actinomycetes*. *Biotechnol Adv* June 15. DOI:10.1016/j.biotechadv.2015.06.003

Lin J, Nishiyama M, & Kuzuyama T (2015) Identification of the biosynthetic gene cluster for the herbicide phosphonothrixin in Saccharothrix sp. ST-888. *J Antibiot* (Tokyo) 68(5):357-359.

Yamazaki T, Pascal S M, Singer A U, Formankay J D, & Kay L E (1995) Nmr Pulse Schemes for the Sequence-Specific Assignment of Arginine Guanidino N-15 and H-1 Chemical-Shifts in Proteins. *J. Am. Chem. Soc.* 117(12):3556-3564.

Platzer G, Okon M, & McIntosh L P (2014) pH-dependent random coil (1)H, (13)C, and (15)N chemical shifts of the ionizable amino acids: a guide for protein pK a measurements. *J. Biomol. NMR* 60(2-3):109-129.

Yavari I & Roberts J D (1978) Differential rates of proton exchange for the guanidinium nitrogens of L-arginine determined by natural-abundance nitrogen-15 nuclear magnetic resonance spectroscopy. *Biochem. Biophys. Res. Commun.* 83(2):635-640.

Clement B, Schnorwangen E, Kampchen T, Mordvintcev P, & Mulsch A (1994) Synthesis of 15N omega-hydroxy-L-arginine and ESR and 15N-NMR studies for the elucidation of the molecular mechanism of enzymic nitric oxide formation from L-arginine. *Arch. Pharm.* (Weinheim) 327(12):793-798.

Bush D R, Wysocki V H, & Scaraffia P Y (2012) Study of the fragmentation of arginine isobutyl ester applied to arginine quantification in *Aedes aegypti* mosquito excreta. *J. Mass. Spectrom.* 47 (10): 1364-1371.

Gehrig P M, Hunziker P E, Zahariev S, & Pongor S (2004) Fragmentation pathways of N(G)-methylated and unmodified arginine residues in peptides studied by ESI-MS/MS and MALDI-MS. *J. Am. Soc. Mass. Spectrom.* 15(2):142-149.

Shek P Y, Zhao J, Ke Y, Siu K W, & Hopkinson A C (2006) Fragmentations of protonated arginine, lysine and their methylated derivatives: concomitant losses of carbon monoxide or carbon dioxide and an amine. *J. Phys. Chem. A* 110(27):8282-8296.

What is claimed is:

1. A method for manufacturing a medicament for treating a bacterial infection in a subject in need thereof, said medicament comprising a phosphonic acid antibiotic, said antibiotic isolated from a bacterial strain of *Actinobacteria* having a gene encoding pepM or a pepM-dependent biosynthetic pathway, said bacterial strain selected via the following steps:
   a) reviving a bacterial strain from a library of lyophilized vials or slants,
   b) isolating the genomic DNA from each strain,
   c) screening the genomic DNA by PCR using four pairs of degenerate primers designed to amplify a 406-bp conserved fragment within bacterial pepM genes (forward: pepMF, CGCCGGCGTCTGCNTNGAR-GAYAA; reverse: pepMR, GGCGCGCATCATGT-GRTTNGCVYA; pepMX, GCGCGCATCATGTGGTTNGCCCADAT; pepMW, GCGCGCATCATGTGGTTNGCRTADAT; pepMZ, GCGCGCATCATGTTGTTNCCCCADAT),
   d) screening the resulting PCR products by electrophoresis to retrieve pepM sequences, and
   e) selecting those strains with the pepM sequences.

2. A method according to claim 1 wherein the phosphonic acid antibiotic is selected from the group consisting of Compound 1

Aminomethylphosphonic acid

Compound 2

Argolaphos A

Compound 3

Argolaphos B

Compound 4

2,3-Dihydroxypropyl phosphonic acid

Compound 5

Valinophos

Compound 6

2,4-Dihydroxy-1,2-oxaphospholane 2-oxide

Compound 7

2-Hydroxy-3-phosphono propanoic acid

Compound 8

Phosphonocystoximic acid

Compound 9

Desmethylphosphinothricin

Compound 10

Phosphinomethylmalic acid

Compound 11

1-Hydroxy-2-aminoethylphosphonic acid

-continued

Compound 12

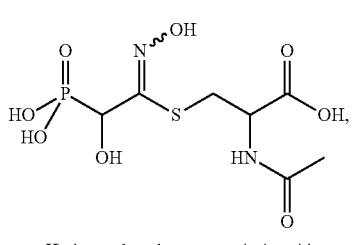

Hydroxyphosphonocystoximic acid

Compound 13

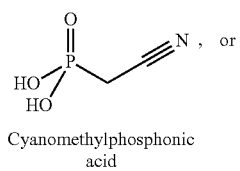

Cyanomethylphosphonic acid

, or

Compound 14

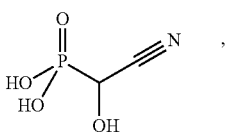

Hydroxycyanomethylphosphonic acid and pharmaceutically acceptable salts, esters, and prodrugs thereof, and mixtures thereof, in the manufacture of a medicament for treating a bacterial infection in a subject in need thereof.

3. A method according to claim 1 comprising the further step of f) isolating the phosphonic acid antibioitc from the selected bacterial strains.

* * * * *